United States Patent
Ly et al.

(10) Patent No.: US 10,117,985 B2
(45) Date of Patent: Nov. 6, 2018

(54) DETERMINING A VOLUME OF MEDICAL FLUID PUMPED INTO OR OUT OF A MEDICAL FLUID CASSETTE

(71) Applicant: Fresenius Medical Care Holdings, Inc., Waltham, MA (US)

(72) Inventors: Tri Ly, Dublin, CA (US); Jie Zhu, Antioch, CA (US); Kulwinder S. Plahey, Martinez, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 974 days.

(21) Appl. No.: 13/972,498

(22) Filed: Aug. 21, 2013

(65) Prior Publication Data
US 2015/0057601 A1 Feb. 26, 2015

(51) Int. Cl.
*A61M 1/28* (2006.01)
*G01F 22/00* (2006.01)
*G01F 22/02* (2006.01)

(52) U.S. Cl.
CPC .............. *A61M 1/28* (2013.01); *A61M 1/281* (2014.02); *A61M 1/288* (2014.02); *G01F 22/00* (2013.01); *G01F 22/02* (2013.01); *A61M 2205/128* (2013.01); *A61M 2205/3379* (2013.01)

(58) Field of Classification Search
CPC ...... A61M 1/16; A61M 1/308; A61M 1/1601; A61M 1/1603; A61M 1/1647; A61M 1/28; A61M 1/306; A61M 1/309; G01F 22/00; G01F 22/02
See application file for complete search history.

(56) References Cited

U.S. PATENT DOCUMENTS

| | | | |
|---|---|---|---|
| 329,773 | A | 11/1885 | Perry |
| 2,383,193 | A | 8/1945 | Herbert |
| 2,529,028 | A | 11/1950 | Landon |
| 2,658,526 | A | 11/1953 | Porter |
| 2,711,134 | A | 6/1955 | Hughes |
| 2,755,745 | A | 7/1956 | Lewis |
| 2,871,795 | A | 2/1959 | Smith |
| 2,886,281 | A | 5/1959 | Canalizo |

(Continued)

FOREIGN PATENT DOCUMENTS

| | | |
|---|---|---|
| DE | 2628238 | 1/1978 |
| DE | 2827648 | 1/1979 |

(Continued)

OTHER PUBLICATIONS

Notification of Transmittal of the International Search Report and the Written Opinion of the International Searching Authority for corresponding PCT Application No. PCT/US2014/048386, dated Oct. 30, 2014, 14 pages.

(Continued)

*Primary Examiner* — Bhisma Mehta
*Assistant Examiner* — William Frehe
(74) *Attorney, Agent, or Firm* — Fish & Richardson P.C.

(57) ABSTRACT

A method that includes pumping medical fluid out of or drawing medical fluid into a chamber of a medical fluid cassette, calculating a theoretical volume of fluid pumped out of or drawn into the chamber, and multiplying the theoretical volume of fluid pumped out of or drawn into the chamber by a correction factor to determine a corrected volume of fluid pumped out of or drawn into the chamber.

19 Claims, 16 Drawing Sheets

(56) References Cited

U.S. PATENT DOCUMENTS

| | | | |
|---|---|---|---|
| 3,083,943 A | 4/1963 | Stewart et al. | |
| 3,323,786 A | 6/1967 | Boschi | |
| 3,556,465 A | 1/1971 | Little | |
| 3,689,025 A | 9/1972 | Kiser | |
| 3,741,687 A | 6/1973 | Nystroem | |
| 3,927,955 A | 12/1975 | Spinosa et al. | |
| 3,966,358 A | 6/1976 | Heimes et al. | |
| 3,985,135 A | 10/1976 | Carpenter et al. | |
| 4,026,669 A | 5/1977 | Leonard et al. | |
| 4,047,844 A | 9/1977 | Robinson | |
| 4,121,584 A | 10/1978 | Turner et al. | |
| 4,152,098 A | 5/1979 | Moody et al. | |
| 4,158,530 A | 6/1979 | Bernstein | |
| 4,178,940 A | 12/1979 | Au | |
| 4,273,121 A | 6/1981 | Jassawalla | |
| 4,303,376 A | 12/1981 | Siekmann | |
| 4,304,260 A | 12/1981 | Turner et al. | |
| 4,322,201 A | 3/1982 | Archibald | |
| 4,333,452 A | 6/1982 | Au | |
| 4,370,983 A | 2/1983 | Lichtenstein | |
| 4,382,753 A | 5/1983 | Archibald | |
| 4,410,322 A | 10/1983 | Archibald | |
| 4,412,553 A | 11/1983 | Kopp et al. | |
| 4,436,620 A | 3/1984 | Bellotti et al. | |
| 4,453,932 A | 6/1984 | Pastrone | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,490,621 A | 12/1984 | Watabe et al. | |
| 4,558,715 A | 12/1985 | Walton et al. | |
| 4,569,378 A | 2/1986 | Bergandy | |
| 4,583,920 A | 4/1986 | Lindner | |
| 4,597,412 A | 7/1986 | Stark | |
| 4,623,328 A | 11/1986 | Hartranft | |
| 4,628,499 A | 12/1986 | Hammett | |
| 4,639,245 A | 1/1987 | Pastrone et al. | |
| 4,643,713 A | 2/1987 | Viitala | |
| 4,657,490 A | 4/1987 | Abbott | |
| 4,662,598 A | 5/1987 | Weingarten | |
| 4,662,906 A | 5/1987 | Matkovich et al. | |
| 4,676,467 A | 6/1987 | Palsulich | |
| 4,690,621 A | 9/1987 | Swain | |
| 4,703,913 A | 11/1987 | Hunkapiller | |
| 4,705,259 A | 11/1987 | Dolhen et al. | |
| 4,710,166 A | 12/1987 | Thompson et al. | |
| 4,735,558 A | 4/1988 | Kienholz et al. | |
| 4,778,451 A | 10/1988 | Kamen | |
| 4,808,161 A * | 2/1989 | Kamen | A61M 5/16809 128/DIG. 12 |
| 4,826,482 A | 5/1989 | Kamen | |
| 4,840,542 A | 6/1989 | Abbott | |
| 4,842,584 A | 6/1989 | Pastrone | |
| 4,846,636 A | 7/1989 | Danby et al. | |
| 4,850,980 A | 7/1989 | Lentz et al. | |
| 4,858,883 A | 8/1989 | Webster | |
| 4,902,282 A | 2/1990 | Bellotti et al. | |
| 4,906,260 A | 3/1990 | Emheiser et al. | |
| 4,927,411 A | 5/1990 | Pastrone et al. | |
| 4,950,134 A | 8/1990 | Bailey et al. | |
| 4,974,754 A | 12/1990 | Wirz | |
| 4,976,162 A | 12/1990 | Kamen | |
| 4,995,864 A | 2/1991 | Bartholomew et al. | |
| 4,997,464 A | 3/1991 | Kopf | |
| 5,002,471 A | 3/1991 | Perlov | |
| 5,006,050 A | 4/1991 | Cooke et al. | |
| 5,036,886 A | 8/1991 | Olsen et al. | |
| 5,061,236 A | 10/1991 | Sutherland et al. | |
| 5,088,515 A | 2/1992 | Kamen | |
| 5,098,262 A | 3/1992 | Wecker et al. | |
| 5,100,380 A | 3/1992 | Epstein et al. | |
| 5,100,699 A | 3/1992 | Roeser | |
| 5,116,021 A | 5/1992 | Faust et al. | |
| 5,116,316 A | 5/1992 | Sertic et al. | |
| 5,146,713 A | 9/1992 | Grafius | |
| 5,151,019 A | 9/1992 | Danby et al. | |
| 5,167,837 A | 12/1992 | Snodgrass et al. | |
| 5,171,029 A | 12/1992 | Maxwell et al. | |
| 5,178,182 A | 1/1993 | Kamen | |
| 5,193,990 A | 3/1993 | Kamen et al. | |
| 5,211,201 A | 5/1993 | Kamen et al. | |
| 5,241,985 A | 9/1993 | Faust et al. | |
| 5,247,434 A | 9/1993 | Peterson et al. | |
| 5,249,932 A | 10/1993 | Van Bork | |
| 5,252,044 A | 10/1993 | Raines et al. | |
| 5,259,352 A | 11/1993 | Gerhardy et al. | |
| 5,279,556 A | 1/1994 | Goi et al. | |
| 5,302,093 A | 4/1994 | Owens et al. | |
| 5,324,422 A | 6/1994 | Colleran et al. | |
| 5,330,425 A | 7/1994 | Utterberg | |
| 5,342,182 A | 8/1994 | Montoya et al. | |
| 5,344,292 A | 9/1994 | Rabenau et al. | |
| 5,350,357 A | 9/1994 | Kamen et al. | |
| D351,470 S | 10/1994 | Scherer et al. | |
| 5,353,837 A | 10/1994 | Faust | |
| 5,378,126 A | 1/1995 | Abrahamson et al. | |
| 5,395,351 A | 3/1995 | Munsch | |
| 5,413,626 A | 5/1995 | Bartsch | |
| 5,415,528 A | 5/1995 | Ogden et al. | |
| 5,421,208 A | 6/1995 | Packard et al. | |
| 5,421,823 A | 6/1995 | Kamen et al. | |
| 5,427,509 A | 6/1995 | Chapman et al. | |
| 5,431,626 A | 7/1995 | Bryant et al. | |
| 5,431,627 A | 7/1995 | Pastrone et al. | |
| 5,431,634 A | 7/1995 | Brown | |
| 5,438,510 A | 8/1995 | Bryant et al. | |
| 5,441,636 A | 8/1995 | Chevallet et al. | |
| 5,445,506 A | 8/1995 | Afflerbaugh et al. | |
| 5,447,286 A | 9/1995 | Kamen et al. | |
| 5,462,416 A | 10/1995 | Dennehey et al. | |
| 5,462,417 A | 10/1995 | Chapman | |
| 5,474,683 A * | 12/1995 | Bryant | A61M 1/28 210/103 |
| 5,478,211 A | 12/1995 | Dominiak et al. | |
| 5,480,294 A | 1/1996 | DiPerna et al. | |
| 5,482,438 A | 1/1996 | Anderson et al. | |
| 5,482,440 A | 1/1996 | Dennehey et al. | |
| 5,482,446 A | 1/1996 | Williamson et al. | |
| 5,484,239 A | 1/1996 | Chapman et al. | |
| 5,486,286 A | 1/1996 | Peterson et al. | |
| 5,514,069 A | 5/1996 | Brown et al. | |
| 5,538,405 A | 7/1996 | Patno et al. | |
| 5,540,568 A | 7/1996 | Rosen et al. | |
| 5,547,453 A | 8/1996 | DiPerna | |
| 5,551,850 A | 9/1996 | Williamson et al. | |
| 5,551,941 A | 9/1996 | Howell | |
| 5,551,942 A | 9/1996 | Brown et al. | |
| 5,554,013 A | 9/1996 | Owens et al. | |
| 5,570,716 A | 11/1996 | Kamen et al. | |
| 5,573,385 A | 11/1996 | Chevallier | |
| 5,578,070 A | 11/1996 | Utterberg | |
| 5,588,816 A | 12/1996 | Abbott et al. | |
| 5,593,290 A | 1/1997 | Greisch et al. | |
| 5,609,572 A | 3/1997 | Lang | |
| 5,614,677 A | 3/1997 | Wamsiedler et al. | |
| 5,628,908 A | 5/1997 | Kamen et al. | |
| 5,630,710 A | 5/1997 | Tune et al. | |
| 5,634,896 A | 6/1997 | Bryant et al. | |
| 5,640,995 A | 6/1997 | Packard et al. | |
| 5,641,405 A | 6/1997 | Keshaviah et al. | |
| 5,641,892 A | 6/1997 | Larkins et al. | |
| 5,643,205 A | 7/1997 | Utterberg | |
| 5,645,531 A | 7/1997 | Thompson et al. | |
| 5,658,133 A | 8/1997 | Anderson et al. | |
| 5,669,764 A | 9/1997 | Behringer et al. | |
| 5,690,602 A | 11/1997 | Brown et al. | |
| D390,654 S | 2/1998 | Alsberg et al. | |
| 5,713,865 A | 2/1998 | Manning et al. | |
| 5,713,888 A | 2/1998 | Neuenfeldt et al. | |
| 5,718,567 A | 2/1998 | Rapp et al. | |
| 5,741,125 A | 4/1998 | Neftel et al. | |
| 5,746,708 A | 5/1998 | Giesler et al. | |
| 5,755,683 A | 5/1998 | Houle et al. | |
| 5,764,034 A | 6/1998 | Bowman et al. | |
| 5,769,387 A | 6/1998 | Perez | |

(56) References Cited

U.S. PATENT DOCUMENTS

| | | |
|---|---|---|
| 5,771,914 A | 6/1998 | Ling et al. |
| 5,772,635 A | 6/1998 | Dastur et al. |
| 5,772,637 A | 6/1998 | Heinzmann et al. |
| 5,775,371 A | 7/1998 | Pan et al. |
| 5,782,575 A | 7/1998 | Vincent et al. |
| 5,782,805 A | 7/1998 | Meinzer et al. |
| 5,799,207 A | 8/1998 | Wang et al. |
| 5,816,779 A | 10/1998 | Lawless et al. |
| 5,840,151 A | 11/1998 | Munsch |
| 5,842,841 A | 12/1998 | Danby et al. |
| 5,843,035 A | 12/1998 | Bowman et al. |
| 5,868,696 A | 2/1999 | Giesler et al. |
| 5,873,853 A | 2/1999 | Keilman et al. |
| 5,902,096 A | 5/1999 | Behringer et al. |
| 5,906,598 A | 5/1999 | Giesler et al. |
| 5,921,951 A | 7/1999 | Morris |
| 5,925,011 A | 7/1999 | Faict et al. |
| 5,934,885 A | 8/1999 | Farrell et al. |
| 5,935,099 A | 8/1999 | Peterson et al. |
| 5,938,634 A | 8/1999 | Packard |
| 5,989,423 A | 11/1999 | Kamen et al. |
| 5,993,174 A | 11/1999 | Konishi |
| 5,996,634 A | 12/1999 | Dennehey et al. |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,053,191 A | 4/2000 | Hussey |
| 6,065,389 A | 5/2000 | Riedlinger |
| 6,065,941 A | 5/2000 | Gray et al. |
| 6,068,612 A | 5/2000 | Bowman et al. |
| 6,074,359 A | 6/2000 | Keshaviah et al. |
| 6,079,959 A | 6/2000 | Kingsford et al. |
| 6,099,492 A | 8/2000 | Le Boeuf |
| 6,106,246 A | 8/2000 | Steck et al. |
| 6,110,410 A | 8/2000 | Owens et al. |
| 6,118,207 A | 9/2000 | Ormerod et al. |
| 6,129,517 A | 10/2000 | Danby et al. |
| 6,132,187 A | 10/2000 | Ericson |
| 6,136,565 A | 10/2000 | Best et al. |
| 6,152,705 A | 11/2000 | Kennedy et al. |
| 6,154,605 A | 11/2000 | Aonuma |
| 6,164,621 A | 12/2000 | Bouchard et al. |
| 6,165,154 A | 12/2000 | Gray et al. |
| 6,168,394 B1 | 1/2001 | Forman et al. |
| 6,178,996 B1 | 1/2001 | Suzuki |
| 6,179,801 B1 | 1/2001 | Holmes et al. |
| 6,184,356 B1 | 2/2001 | Anderson et al. |
| 6,189,857 B1 | 2/2001 | Zeger et al. |
| 6,196,987 B1 | 3/2001 | Holmes et al. |
| 6,200,287 B1 | 3/2001 | Keller et al. |
| 6,206,644 B1 | 3/2001 | Pereira et al. |
| 6,208,107 B1 | 3/2001 | Maske et al. |
| 6,210,361 B1 | 4/2001 | Kamen et al. |
| 6,220,295 B1 | 4/2001 | Bouchard et al. |
| 6,223,130 B1 | 4/2001 | Gray et al. |
| 6,227,807 B1 | 5/2001 | Chase |
| 6,227,824 B1 | 5/2001 | Stehr |
| 6,228,047 B1 | 5/2001 | Dadson |
| 6,229,753 B1 | 5/2001 | Kono et al. |
| 6,231,537 B1 | 5/2001 | Holmes et al. |
| 6,234,989 B1 | 5/2001 | Brierton et al. |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,286,566 B1 | 9/2001 | Cline et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,315,707 B1 | 11/2001 | Smith et al. |
| 6,315,754 B1 | 11/2001 | Daoud et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,367,669 B1 | 4/2002 | Au et al. |
| 6,382,923 B1 | 5/2002 | Gray |
| 6,383,158 B1 | 5/2002 | Utterberg et al. |
| 6,402,486 B1 | 6/2002 | Steck et al. |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,484,383 B1 | 11/2002 | Herklotz |
| 6,489,896 B1 | 12/2002 | Platt et al. |
| 6,491,656 B1 | 12/2002 | Morris |
| 6,494,694 B2 | 12/2002 | Lawless et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,529,573 B2 | 3/2003 | Olsher et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,579,253 B1 | 6/2003 | Burbank et al. |
| 6,592,542 B2 | 7/2003 | Childers et al. |
| 6,595,948 B2 | 7/2003 | Suzuki et al. |
| 6,603,229 B1 | 8/2003 | Toye |
| 6,604,908 B1 | 8/2003 | Bryant et al. |
| 6,645,166 B2 | 11/2003 | Scheunert et al. |
| 6,645,177 B1 | 11/2003 | Shearn |
| 6,648,861 B2 | 11/2003 | Platt et al. |
| 6,663,359 B2 | 12/2003 | Gray |
| 6,670,323 B1 | 12/2003 | Looker et al. |
| 6,672,841 B1 | 1/2004 | Herklotz et al. |
| 6,695,593 B1 | 2/2004 | Steck et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Dönig et al. |
| 6,746,514 B2 | 6/2004 | Bedingfield et al. |
| 6,749,403 B2 | 6/2004 | Bryant et al. |
| 6,752,172 B2 | 6/2004 | Lauer |
| 6,752,599 B2 | 6/2004 | Park |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,759,014 B2 | 7/2004 | Dales et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,014 B2 | 9/2004 | Bowen |
| 6,790,195 B2 | 9/2004 | Steele et al. |
| 6,790,198 B2 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |
| 6,852,090 B2 | 2/2005 | Burbank et al. |

(56) References Cited

U.S. PATENT DOCUMENTS

| | | |
|---|---|---|
| 6,869,538 B2 | 3/2005 | Yu et al. |
| 6,905,479 B1 | 6/2005 | Bouchard et al. |
| 6,929,751 B2 | 8/2005 | Bowman et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,957,952 B1 | 10/2005 | Steck et al. |
| 6,984,218 B2 | 1/2006 | Nayak et al. |
| 7,021,148 B2 | 4/2006 | Kuhn et al. |
| 7,029,245 B2 | 4/2006 | Maianti et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman et al. |
| 7,195,607 B2 | 3/2007 | Westberg et al. |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,261,559 B2 | 8/2007 | Smith et al. |
| 7,267,661 B2 | 9/2007 | Susi |
| 7,273,465 B2 | 9/2007 | Ash |
| 7,306,578 B2 | 12/2007 | Gray et al. |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,461,968 B2 | 12/2008 | Demers et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,286 B2 | 2/2010 | Childers et al. |
| 7,699,966 B2 | 4/2010 | Qin et al. |
| 7,717,682 B2 | 5/2010 | Orr |
| 7,776,006 B2 | 8/2010 | Childers et al. |
| 7,789,849 B2 | 9/2010 | Busby et al. |
| 7,815,595 B2 | 10/2010 | Busby et al. |
| 7,909,795 B2 * | 3/2011 | Childers ............... A61M 1/28 604/131 |
| 8,038,640 B2 | 10/2011 | Orr |
| 8,197,231 B2 | 6/2012 | Orr |
| 8,197,439 B2 | 6/2012 | Wang et al. |
| 8,206,338 B2 | 6/2012 | Childers et al. |
| 8,292,594 B2 | 10/2012 | Tracey et al. |
| 8,366,921 B2 | 2/2013 | Beden et al. |
| 2001/0034502 A1 | 10/2001 | Moberg et al. |
| 2001/0037763 A1 | 11/2001 | Deguchi et al. |
| 2002/0045851 A1 | 4/2002 | Suzuki et al. |
| 2002/0062109 A1 | 5/2002 | Lauer |
| 2002/0072718 A1 | 6/2002 | Brugger et al. |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0194332 A1 | 10/2003 | Jahn et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0001766 A1 | 1/2004 | Maianti et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0109769 A1 | 6/2004 | Jahn et al. |
| 2004/0115068 A1 | 6/2004 | Hansen et al. |
| 2004/0135078 A1 | 7/2004 | Mandro et al. |
| 2004/0136843 A1 | 7/2004 | Jahn et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0230292 A1 | 10/2005 | Beden et al. |
| 2006/0002823 A1 | 1/2006 | Feldstein |
| 2006/0079826 A1 | 4/2006 | Beden et al. |
| 2006/0195064 A1 | 8/2006 | Plahey et al. |
| 2007/0077156 A1 | 4/2007 | Orr |
| 2007/0112297 A1 | 5/2007 | Plahey et al. |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2008/0015793 A1 | 1/2008 | Ben-Menahem et al. |
| 2008/0033346 A1 | 2/2008 | Childers et al. |
| 2008/0077068 A1 | 3/2008 | Orr |
| 2008/0125693 A1 | 5/2008 | Gavin et al. |
| 2008/0208103 A1 | 8/2008 | Demers et al. |
| 2008/0216898 A1 | 9/2008 | Grant et al. |
| 2008/0253912 A1 | 10/2008 | Demers et al. |
| 2009/0004033 A1 | 1/2009 | Demers et al. |
| 2009/0099498 A1 | 4/2009 | Demers et al. |
| 2009/0137940 A1 | 5/2009 | Orr |
| 2009/0215602 A1* | 8/2009 | Min ................... A61M 1/3693 494/4 |
| 2010/0241062 A1* | 9/2010 | Morris ................... A61M 1/14 604/29 |
| 2011/0092895 A1 | 4/2011 | Yardimci et al. |
| 2011/0125085 A1 | 5/2011 | McGill et al. |
| 2011/0137237 A1 | 6/2011 | Prisco et al. |
| 2012/0065581 A1 | 3/2012 | Childers et al. |
| 2012/0123322 A1 | 5/2012 | Scarpaci et al. |
| 2012/0224984 A1 | 9/2012 | Orr |
| 2012/0271226 A1* | 10/2012 | Farrell ................... A61M 1/28 604/29 |
| 2012/0308412 A1 | 12/2012 | Rochat |
| 2013/0184638 A1 | 7/2013 | Scarpaci et al. |

FOREIGN PATENT DOCUMENTS

| | | |
|---|---|---|
| DE | 4006785 | 9/1990 |
| DE | 4336336 | 5/1994 |
| DE | 19837667 | 3/2000 |

(56) References Cited

FOREIGN PATENT DOCUMENTS

| | | |
|---|---|---|
| DE | 19919572 A1 | 11/2000 |
| DE | 10042324 | 2/2002 |
| DE | 10046651 | 4/2002 |
| DE | 19919572 C2 | 4/2002 |
| DE | 10053441 | 5/2002 |
| DE | 69618766 | 8/2002 |
| DE | 10143137 | 4/2003 |
| DE | 10157924 | 6/2003 |
| DE | 102007059239 | 6/2009 |
| EP | 0314379 | 8/1991 |
| EP | 0410125 B1 | 8/1993 |
| EP | 0728509 | 8/1996 |
| EP | 0848193 | 6/1998 |
| EP | 0856321 | 8/1998 |
| EP | 0947814 B2 | 10/1999 |
| EP | 0956876 A1 | 11/1999 |
| EP | 1529545 | 5/2005 |
| GB | 2101232 A | 1/1983 |
| GB | 1483702 | 8/1997 |
| GB | 2331796 | 6/1999 |
| JP | 0396850 A | 4/1991 |
| JP | 04191755 | 7/1992 |
| JP | 06154314 | 6/1994 |
| JP | 06002650 | 11/1994 |
| JP | 08028722 | 3/1996 |
| JP | 11347115 | 12/1999 |
| JP | 2000070358 | 3/2000 |
| JP | 2000346214 | 12/2000 |
| WO | 8402473 | 7/1984 |
| WO | 8601115 | 2/1986 |
| WO | WO1994015660 A1 | 7/1994 |
| WO | 9420155 | 9/1994 |
| WO | 9625064 A2 | 8/1996 |
| WO | 1997016214 | 5/1997 |
| WO | 1997037703 | 10/1997 |
| WO | 9822165 | 5/1998 |
| WO | WO1998022167 A1 | 5/1998 |
| WO | 0023140 | 4/2000 |
| WO | 0033898 | 6/2000 |
| WO | 0117605 | 3/2001 |
| WO | 0225146 | 3/2002 |
| WO | 0225225 | 3/2002 |
| WO | WO2007006030 A3 | 6/2007 |
| WO | 2009071069 | 6/2009 |
| WO | WO2011045167 A1 | 4/2011 |
| WO | WO 2012172398 A1 * | 12/2012 ............ A61M 1/16 |

OTHER PUBLICATIONS

Avolio, Glenn, "Principles of Rotary Optical Encoders," Sensors Journal of Machine Perception, vol. 10, No. 4, pp. 10-18, 1993.

Gambro®, "DEHP-free cartridge blood sets," © Nov. 2004, Gambro, Inc., Lakewood, CO, 4 pp.

Gambro®, "Prisma® HF 1000, For Increased Filtration Capacity", © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prismaflex™ anticipating critical care needs and taking our innovative response . . . to new heights," © 2004, Gambro, Inc., Lakewood, CO, 8 pp.

Liberty Cycler Operator's Manual, 2003-2004.

Manns et al., "The acu-men: A new device for continuous renal replacement therapy in acute renal failure," Kidney International, vol. 54, pp. 268-274, 1998.

Newton IQ Cycler Operator Manual, Part No. 470203 Rev. F, 2000-2006.

Operator's Instructions, Fresenius 90/2 Peritoneal Therapy Cycler, Part No. 470016, Rev. B, 1991.

Operator's Manual, Serena, Program Version 3.xx—English, 2002.

Sleep Safe Operating Instructions, Software Version 0.9, Part No. 677 801 1; Aug. 2000.

Sleep Safe Technical Manual, Part No. 677 807 1; Aug. 2000.

Bolegoh, Gordon, "Pumps: Reference Guide", p. 24, 3rd edition, 2001.

Ronco et al., "Evolution of Machines for Automated Peritoneal Dialysis", in Automated Peritoneal Dialysis, Contributions to Nephrology, vol. 129, pp. 142-161, 1999.

Sleep Safe Operating Instructions, Software Version 0.5, Apr. 1999.

Sleep Safe Operating Instructions, Software Version 1.0, Oct. 2000.

Sleep Safe Technical Manual, Dec. 2001.

Sleep Safe Operating Instructions, Jan. 2002.

Sleep Safe Communicating Therapy, Mar. 1998.

Sleep Safe Kommunizierte Therapie, May 1998.

Innovative Technologies in Peritoneal Dialysis, Sleep Safe Concept, Oct. 13, 1999 (4 attachments).

TL™ Pump Brochure, TL Systems Corporation, Apr. 1975.

* cited by examiner

DETERMINING A VOLUME OF MEDICAL FLUID PUMPED INTO OR OUT OF A MEDICAL FLUID CASSETTE

TECHNICAL FIELD

This disclosure relates to determining a volume of medical fluid pumped into or out of a medical fluid cassette.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect, a method includes (a) pumping medical fluid out of or drawing medical fluid into a chamber of a medical fluid cassette, (b) calculating a theoretical volume of fluid pumped out of or drawn into the chamber, and (c) multiplying the theoretical volume of fluid pumped out of or drawn into the chamber by a correction factor to determine a corrected volume of fluid pumped out of or drawn into the chamber.

In another aspect, a medical fluid pumping system includes a medical fluid cassette including a flexible membrane that at least partially defines a pump chamber and a medical fluid pumping machine defining a compartment configured to receive the medical fluid cassette. The medical fluid pumping machine includes a piston that is aligned with the pump chamber of the medical fluid cassette when the medical fluid cassette is disposed within the compartment. The piston is operable to pump medical fluid out of or draw medical fluid into the pump chamber of the medical fluid cassette. The medical fluid pumping machine also includes a control unit that is operable to calculate a theoretical volume of fluid pumped out of or drawn into the pump chamber and that is operable to multiply the theoretical volume of fluid pumped out of or drawn into the pump chamber by a correction factor to determine a corrected volume of fluid pumped out of or drawn into the pump chamber.

Implementations can include one or more of the following features.

In some implementations, the method further includes multiplying the theoretical volume by the correction factor to determine an adjustment volume.

In certain implementations, the adjustment volume is added to the theoretical volume to determine the corrected volume.

In some implementations, the medical fluid cassette includes a flexible membrane that at least partially defines the chamber.

In certain implementations, the medical fluid cassette includes a rigid base that cooperates with the flexible membrane to at least partially form the chamber.

In some implementations, the medical fluid cassette includes a fastening member attached to the flexible membrane. The fastening member defines a recess configured to receive a piston head of a medical fluid pumping machine, and the fastening member has an engagement surface that engages an engagement surface of the piston head when the piston head is disposed in the recess such that, when the piston head is disposed in the recess and is moved linearly away from the base of the cassette, the engagement surface of the piston head is engaged with the engagement surface of the fastening member and pulls the fastening member and the flexible membrane to which the fastening member is attached away from the base to increase a volume of the fluid pump chamber.

In certain implementations, pumping the medical fluid out of the chamber includes driving the membrane of the medical fluid cassette to decrease a volume of the chamber, and drawing the medical fluid into the chamber includes driving the membrane of the medical fluid cassette to increase the volume of the chamber.

In some implementations, the method further includes driving a fastening member that is attached to the membrane. The fastening member is configured to mechanically couple to a piston.

In certain implementations, the membrane is driven by a piston.

In some implementations, the piston includes a piston head attached to a piston shaft.

In certain implementations, the piston head is substantially dome-shaped or mushroom head shaped.

In some implementations, at least a portion of the piston head has an outer diameter that is less than a maximum inner diameter of a recessed region of the rigid base that cooperates with the membrane to form the chamber.

In certain implementations, the method includes pumping medical fluid out of the chamber of the medical fluid cassette by driving a piston against a membrane of the medical fluid cassette to decrease a volume of the chamber, calculating the theoretical volume of fluid pumped out of the chamber, and multiplying the theoretical volume of fluid pumped out of the chamber by the correction factor to determine the corrected volume of fluid pumped out of the chamber.

In some implementations, the method includes drawing medical fluid into the chamber of the medical fluid cassette by retracting a piston to pull a membrane of the medical fluid cassette to increase a volume of the chamber, calculating the theoretical volume of fluid drawn into the chamber, and multiplying the theoretical volume of fluid drawn into the chamber by the correction factor to determine the corrected volume of fluid drawn into the chamber.

In certain implementations, the method includes repeating steps (a)-(c) (listed in the first paragraph of this section) multiple times during the course of a dialysis treatment and summing the determined corrected volumes to determine a total corrected volume of fluid pumped out of or drawn into the chamber over the course of the dialysis treatment.

In some implementations, the dialysis treatment includes pumping dialysate out of the pump chamber and into a peritoneal cavity of a patient multiple times and drawing dialysate out of the peritoneal cavity of the patient and into the pump chamber multiple times, and the method includes carrying out steps (a)-(c) each time the dialysate is pumped out of the pump chamber and into the peritoneal cavity of the patient and each time the dialysate is drawn out of the peritoneal cavity of the patient and into the pump chamber to determine a total volume of dialysate delivered to the peritoneal cavity of the patient and a total volume of dialysate removed from the peritoneal cavity of the patient during the treatment.

In certain implementations, calculating the theoretical volume of fluid pumped out of or drawn into the chamber includes determining a linear displacement of a piston.

In some implementations, determining the linear displacement of the piston includes determining a number of turns of a stepper motor operatively connected to the piston.

In certain implementations, the method further includes measuring a pressure of medical fluid within the medical fluid cassette or within a fluid line connected to the medical fluid cassette.

In some implementations, the method further includes isolating the pump chamber prior to measuring the pressure.

In certain implementations, isolating the pump chamber includes closing valves adjacent first and second ports of the pump chamber.

In some implementations, the pressure is measured a period of time (e.g., 0.5 seconds) after isolating the pump chamber.

In certain implementations, the pump chamber is isolated and the pressure is measured after drawing medical fluid into the pump chamber.

In some implementations, the pump chamber is isolated and the pressure is measured after pumping medical fluid out of the pump chamber.

In certain implementations, the method further includes selecting the correction factor based on the measured pressure.

In some implementations, the coefficient factor varies as a function of measured pressure for measured pressures between a first pressure value and a second pressure value, and the first pressure value is less than the second pressure value.

In certain implementations, when the measured pressure is between the first and second pressure values, the coefficient factor is determined using the following equation:

$$((\text{measured pressure}-30)*2/5)/10.$$

In some implementations, when the measured pressure is between the first and second pressure values, the coefficient factor is determined using the following equation:

$$(15-(\text{measured pressure}+40)*15/80)/10.$$

In certain implementations, the coefficient factor is a first constant for all measured pressures that are less than or equal to the first pressure value and the coefficient factor is a second constant for all measured pressures that are greater than or equal to the second pressure value.

In some implementations, the first constant is 0 and the second constant is 0.02.

In certain implementations, the first pressure value is 30 mbar and the second pressure value is 80 mbar.

In some implementations, the first constant is 0.015 and the second constant is 0.

In certain implementations, the first pressure value is −40 mbar and the second pressure value is 40 mbar.

In some implementations, the coefficient factor has a first value if the measured pressure is less than or equal to a first pressure value and the coefficient factor has a second value if the measured pressure is greater than or equal to a second pressure value.

In certain implementations, the coefficient factor has a third value if the measured pressure is greater than the first pressure value and less than the second pressure value.

In some implementations, the coefficient factor has the first value for all measured pressures less than or equal to the first pressure value, and the first value is a constant.

In certain implementations, the coefficient factor has the second value for all measured pressures greater than or equal to the second pressure value, and the second value is a constant.

In some implementations, the first pressure value is 30 mbar.

In certain implementations, the second pressure value is 80 mbar.

In some implementations, the first pressure value is −40 mbar.

In certain implementations, the second pressure value is 40 mbar.

Implementations can include one or more of the following advantages.

Methods described herein can be used to accurately determine the volume of medical fluid pumped out of or drawn into a chamber of a medical fluid cassette. Some such methods, for example, account for a portion of the membrane of the medical fluid cassette that overlies the chamber and bulges outward and inward as pressure within the chamber increases and decreases, respectively. Bulging of the membrane changes the volume of the chamber (as compared to theoretical volume calculations that assume no such bulging of the membrane takes place) and can thus result in inaccuracies of fluid volumes that are determined using a calculation that assumes no such bulging of the membrane occurs. By accounting for bulging of the membrane (e.g., by multiplying a theoretical fluid volume calculation that assumes no bulging of the membrane by a correction factor to determine an adjustment volume and then adding the adjustment volume to the theoretical volume), the volume of fluid pumped out of or drawn into the chamber can be more accurately determined.

In some implementations, the correction factor by which the theoretical fluid volume calculation is multiplied is selected based on the pressure of the medical fluid in the cassette (e.g., the chamber of the cassette). It has been found that the degree to which the cassette membrane overlying the chamber bulges changes as the pressure of the medical fluid within the chamber changes. Therefore, selecting the correction factor based on the pressure of the medical fluid within the chamber can increase the accuracy with which the volume of medical pumped out of or drawn into the chamber is determined.

In certain implementations, the correction factors used during the drain phase of a treatment (i.e., the phase during which medical fluid is drawn out of the patient and into the chamber of the medical fluid cassette and then pumped from the chamber to a drain or drain bag) differ from the correction factors used during the fill phase of the treatment (i.e., the phase during which medical fluid is drawn into the chamber of the medical fluid cassette from a medical fluid source and then pumped from the chamber to the patient). It has been found that the tendency of the cassette membrane to bulge and the degree to which the cassette membrane bulges differs from the drain phase to the fill phase. By using different coefficient factors for these phases, the accuracy with which the volume of medical fluid pumped out of and drawn into the chamber of the medical fluid cassette throughout the treatment can be increased.

In some implementations, the correction factor by which the theoretical volume is multiplied to determine the corrected volume (e.g., to determine an adjustment volume that is used to calculate the corrected volume) is a constant for those pump strokes where the measured pressure is below a minimum pressure limit or above a maximum pressure limit but varies for those pump strokes where the measured pressure falls between the minimum and maximum pressures. It has been found that the degree to which the cassette membrane deforms varies little across relative low and relatively high pressure ranges but varies more significantly across an intermediate pressure range. Thus, using constant correction factors for those pump strokes where the measured pressure falls below a minimum pressure or above a maximum pressure can simplify the determination of the corrected volume without significantly affecting the accuracy of the corrected volume. Using a correction factor that varies based on pressure for those pump strokes where the measured pressure falls between the minimum and maximum pressures helps to ensure the accuracy of the corrected volume.

In certain implementations, a piston is used to drive the membrane of the cassette to pump medical fluid out of the chamber and to draw medical fluid into the chamber. The use of a mechanically operated piston pump as compared to a hydraulic pump can be advantageous because mechanically operated piston pumps tend to be less complex and less expensive than hydraulic pumps. As discussed above, using methods described herein can also increase the accuracy with which the volume of medical fluid pumped out of and drawn into the chamber of the cassette is determined. Thus, certain systems described herein can be less complex and less expensive than systems using hydraulic pumps while achieving comparable volumetric pumping accuracy.

Other aspects, features, and advantages will be apparent from the description and drawings, and from the claims.

DETAILED DESCRIPTION

Figure 1:
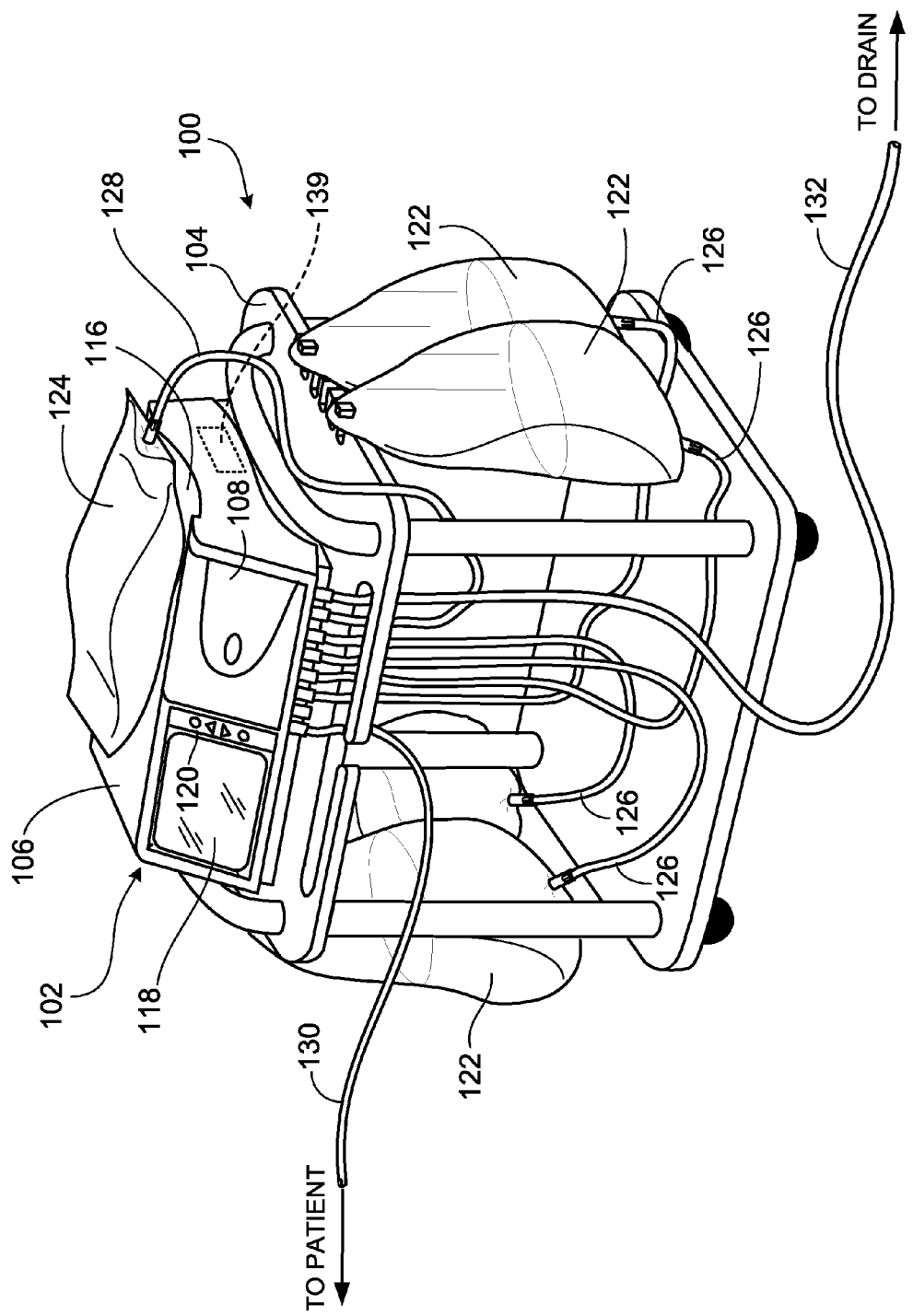
FIG. 1 is a perspective view of a peritoneal dialysis ("PD") system that includes a PD cycler positioned atop a portable cart.
Figure 2:
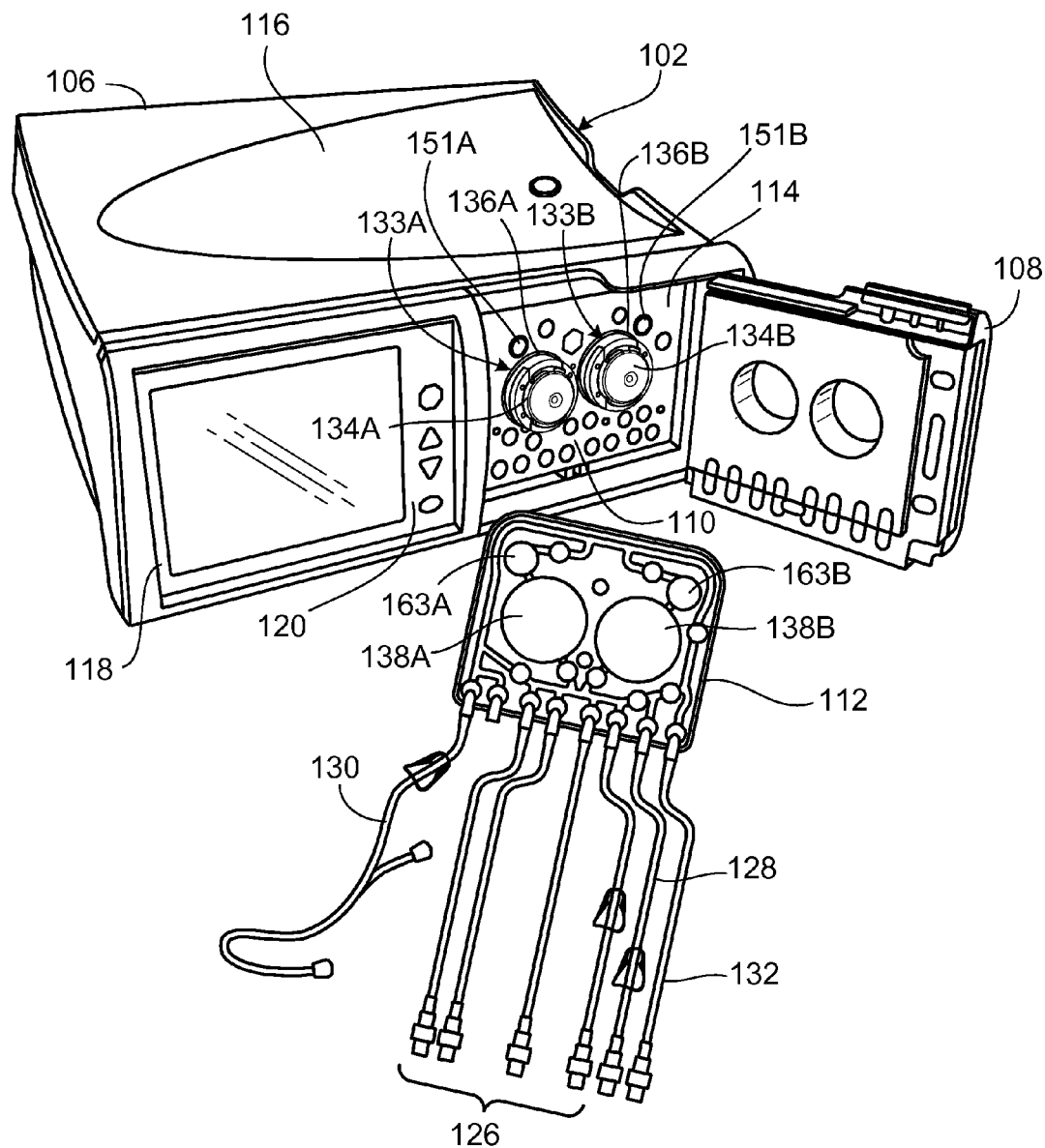
FIG. 2 is a perspective view of the PD cycler and a PD cassette of the PD system of FIG. 1, with a door of the PD cycler in the open position to show the inner surfaces of the PD cycler that interface with the PD cassette during use.

Referring to FIG. 1, a peritoneal dialysis ("PD") system 100 includes a PD cycler (also referred to as a PD machine) 102 seated on a cart 104. Referring also to FIG. 2, the PD cycler 102 includes a housing 106, a door 108, and a cassette interface 110 that contacts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysate (e.g., a 5 liter bag of dialysate). The PD cycler 102 also includes a touch screen 118 and additional control buttons 26 that can be operated by a user (e.g., a patient) to allow, for example, set-up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient during use. The drain line 132 can be connected to a drain or drain receptacle and can be used to pass dialysate from the cassette 112 to the drain or drain receptacle during use.

Figure 3:
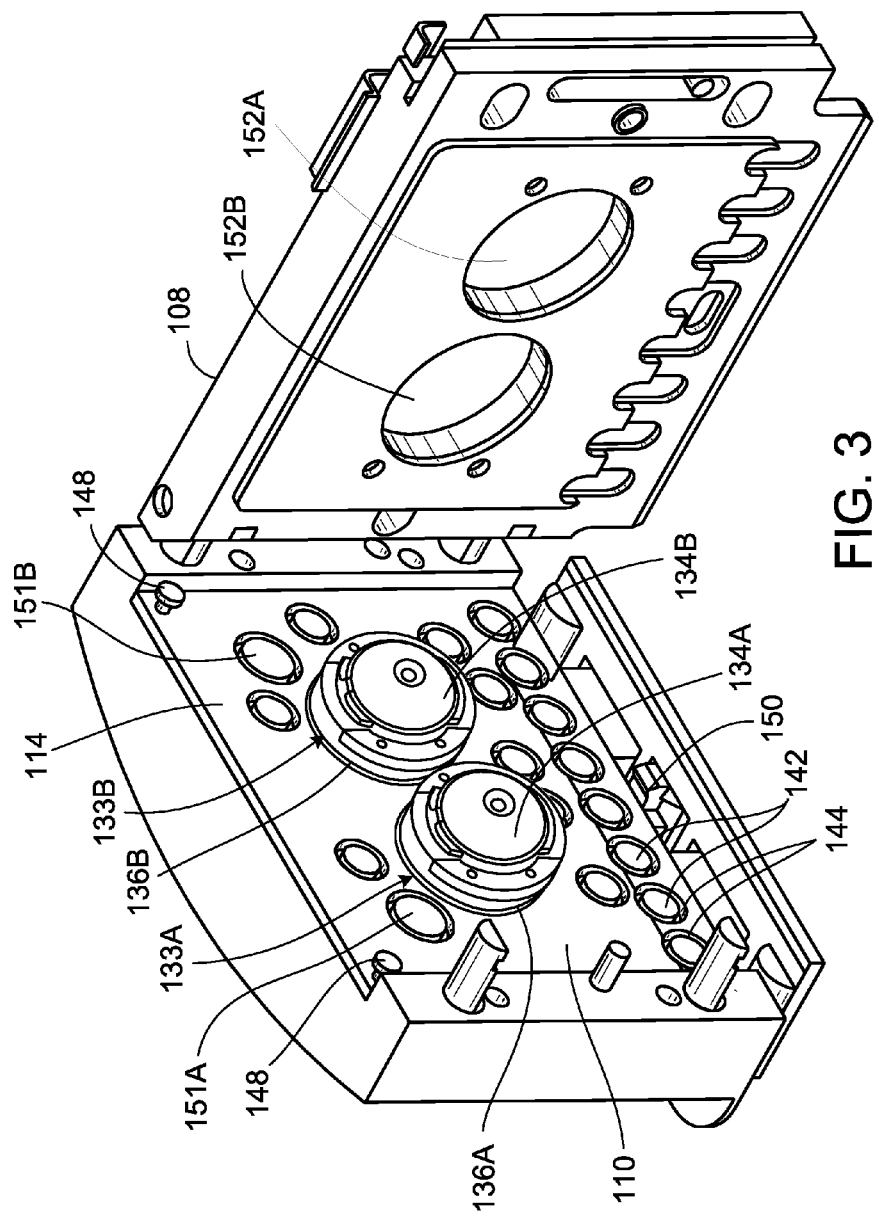
FIG. 3 is a perspective view of an open cassette compartment of the PD cycler of FIG. 1, showing, among other things, pistons having piston heads that include spring loaded latch mechanisms that can be used to mechanically connect the piston heads to associated dome-shaped members of the PD cassette.

FIG. 3 shows a more detailed view of the cassette interface 110 and the door 108 of the PD cycler 102. As shown, the PD cycler 102 includes pistons 133A, 133B with piston heads 134A, 134B attached to piston shafts 135A, 135B (piston shaft 135A shown in FIGS. 9A-9G) that can be axially moved within piston access ports 136A, 136B formed in the cassette interface 110. The piston shafts 135A, 135B are connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward along the lead screws. The nuts, in turn, are connected to the pistons 133A, 133B and thus cause the pistons 133A, 133B to move inward and outward as the stepper motors rotate the lead screws. Stepper motor controllers provide the necessary current to be driven through the windings of the stepper motors to move the pistons 133A, 133B. The polarity of the current determines whether the pistons 133A, 133B are advanced or retracted. In some implementations, the stepper motors require 200 steps to make a full rotation, and this corresponds to 0.048 inch of linear travel.

The PD system 100 also includes encoders (e.g., optical encoders) that measure the rotational movement of the lead screws. The axial positions of the pistons 133A, 133B can be determined based on the rotational movement of the lead screws, as determined by the encoders. Thus, the measurements of the encoders can be used to very accurately position the piston heads 134A, 134B of the pistons 133A, 133B.

As discussed below, when the cassette 112 (shown in FIGS. 2 and 4-7) is positioned within the cassette compartment 114 of the PD cycler 102 with the door 108 closed, the piston heads 134A, 134B of the PD cycler 102 align with pump chambers 138A, 138B of the cassette 112 such that the piston heads 134A, 134B can be mechanically connected to fastening members of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B, while retraction of the piston heads 134A, 134B away from the cassette 112 can increase the volume of the pump chambers 138A, 138B and cause dialysate to be drawn into the pump chambers 138A, 138B.

As shown in FIG. 3, the cassette interface 110 includes two pressure sensors 151A, 151B that align with pressure sensing chambers 163A, 163B (shown in FIGS. 2, 4, 6, and 7) of the cassette 112 when the cassette 112 is positioned within the cassette compartment 114. Portions of a membrane 140 of the cassette 112 that overlie the pressure sensing chambers 163A, 163B adhere to the pressure sensors 151A, 151B using vacuum pressure. Specifically, clearance around the pressure sensors 151A, 151B communicates vacuum to the portions of the cassette membrane 140 overlying the pressure sensing chambers 163A, 163B to hold those portions of the cassette membrane 140 tightly against the pressure sensors 151A, 151B. The pressure of fluid within the pressure sensing chambers 163A, 163B causes the portions of the cassette membrane 140 overlying the pressure sensing chambers 163A, 163B to contact and apply pressure to the pressure sensors 151A, 151B. The pressure sensors 151A, 151B can be any sensors that are capable of sensing the fluid pressure in the sensing chambers 163A, 163B. In some implementations, for example, the pressure sensors are solid state silicon diaphragm infusion pump force/pressure transducers. One example of such a sensor is the Model 1865 force/pressure transducer manufactured by Sensym Foxboro ICT. In certain implementations, the force/pressure transducers are modified to provide increased voltage output. The force/pressure transducers can, for example, be modified to produce an output signal of 0 to 5 volts.

Still referring to FIG. 3, the PD cycler 102 also includes multiple inflatable members 142 positioned within inflatable member ports 144 in the cassette interface 110. The inflatable members 142 align with depressible dome regions 146 of the cassette 112 (shown in FIGS. 4-6) when the cassette 112 is positioned within the cassette compartment 114 of the PD cycler 102. While only a couple of the inflatable members 142 are labeled in FIG. 3, it should be understood that the PD cycler 102 includes an inflatable member associated with each of the depressible dome regions 146 of the cassette 112. The inflatable members 142 act as valves to direct dialysate through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member ports 144 and out of contact with the cassette 112 when deflated. By inflating certain inflatable members 142 to depress their associated dome regions 146 on the cassette 112, certain fluid flow paths within the cassette 112 can be occluded. Thus, dialysate can be pumped through the cassette 112 by actuating the piston heads 134A, 134B, and can be guided along desired flow paths within the cassette 112 by selectively inflating and deflating the various inflatable members 142.

Still referring to FIG. 3, locating pins 148 extend from the cassette interface 110 of the PD cycler 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD cycler 102, as shown in FIG. 3, defines cylindrical recesses 152A, 152B that substantially align with the pistons 133A, 133B when the door 108 is in the closed position. When the cassette 112 (shown in FIGS. 4-7) is positioned within the cassette compartment 114, hollow projections 154A, 154B of the cassette 112, inner surfaces of which partially define the pump chambers 138A, 138B, fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the projections 154A, 154B of the cassette 112 and the planar surface of the door 108 supports the other regions of the cassette 112. The door 108 can counteract the forces applied by the inflatable members 142 and thus allows the inflatable members 142 to actuate the depressible dome regions 146 on the cassette 112. The engagement between the door 108 and the hollow projections 154A, 154B of the cassette 112 can also help to hold the cassette 112 in a desired fixed position within the cassette compartment 114 to further ensure that the pistons 133A, 133B align with the fluid pump chambers 138A, 138B of the cassette 112.

A control unit (e.g., microprocessor) 139 (shown in FIG. 1) is connected to the pressure sensors 151A, 151B, to the stepper motors (e.g., the drivers of the stepper motors) that drive the pistons 133A, 133B, and to the encoders that monitor rotation of the lead screws of the stepper motors such that the control unit 139 can receive signals from and transmit signals to those components of the system. In some implementations, the control unit 139 is an MPC823 PowerPC device manufactured by Motorola, Inc. The control unit 139 is programmed to determine the theoretical volumes of fluid pumped out of and drawn into the pump chambers 138A, 138B. In certain implementations, the control unit 139 is programmed to mathematically determine theoretical volumes of fluid pumped out of and drawn into the pump chambers 138A, 138B based on the positions of the pistons 133A, 133B, the volumes of the piston heads 134A, 134B, and the known starting volumes of the pump chambers 138A, 138B. As will be discussed in greater detail below, at the beginning of each outward pump stroke, the pump chamber 138A, 138B is isolated by closing valves (i.e., depressible dome regions 146) on the inlet and outlet sides of the pump chamber 138A, 138B. As the piston 133A, 133B is advanced, the fluid pressure within the pump chamber 138A, 138B is monitored by its corresponding pressure sensor 151A, 151B. When the pressure sensor 151A, 151B detects a reference pressure (e.g., 300 mbar), which is indicative of liquid (rather than air) being pressurized within the pump chamber 138A, 138B, the control unit 139 determines the position of the piston 133A, 133B that corresponds to that pressure. Based on the known geometries of the piston head 134A, 134B and the recessed region of the base that forms the pump chamber 138A, 138B, the position of the piston head 133A, 133B can be used to calculate the pump chamber volume (i.e., the volume of liquid in the pump chamber).

As an alternative to programming the control unit 139 to mathematically determine or calculate the volume of fluid in the pump chamber, in certain implementations, the control unit simply accesses a look-up table that provides the theoretical volume based on the known positions of the pistons 133A, 133B. When the pump chamber 138A, 138B has been isolated in the manner discussed above and the pressure sensor 151A, 151B detects the reference pressure (e.g., 300 mbar), which is indicative of liquid (rather than air) being pressurized within the pump chamber 138A, 138B, the control unit 139 determines the position of the piston 133A, 133B that corresponds to that pressure. It is that position of the piston 133A, 133B that is used when consulting the look-up table to determine the theoretical volume of fluid in the pump chamber 138A 138B.

In order to populate the look-up table with relevant data, the volume of fluid in the pump chamber 138A, 138B can be mathematically determined (based on the known geometries of the piston head 134A, 134B and the recessed region of the base that forms the pump chamber 138A, 138B) for various different positions of the pistons 133A, 133B. Once the look-up table is populated in this manner, the control unit 139 need only determine the position of the piston 133A, 133B to figure out the theoretical volume of dialysate in the pump chamber 138A, 138B in a single step, rather than having to perform numerous mathematical computations during each piston stroke.

As an alternative to populating the look-up table with theoretical volumes that are mathematically determined, the look-up table can be populated with theoretical volumes that are empirically determined. For example, prior to treatment, the PD system can be set up to pump liquid from the pump chamber 138A, 138B to a drain bag sitting on a weight scale that is level with the PC cycler 102. The control unit 139 monitors the piston position for various different piston strokes and monitors the weight of the drain bag after each piston stroke. The fluid volume pumped to the drain bag as a result of each piston stroke is then determined based on the known weight of fluid that was pumped to the bag. This process is repeated numerous times for each starting position of the piston to increase the accuracy of the approximated fluid volume. In this way, the known starting position of the piston can be matched with the determined corresponding fluid volume in the look-up table.

The control unit is also programmed to adjust the determined theoretical volumes of fluid based on pressure signals received from the pressure sensors 151A, 151B. Specifically, the control unit 139 is programmed to multiply the determined theoretical volumes of fluid by a correction factor, which is selected as a function of the pressure measured by one of the pressure sensors 151A, 151B, to determine an adjustment volume. The pressure used to determine the correction factor is the pressure in the isolated pump chamber 138A, 138B at the end of the inward piston stoke during drain and at the end of the outward piston stroke during fill. After determining the adjustment volume, the control unit 139 adds the adjustment volume to the determined theoretical volume to determine a corrected volume. The corrected volume accounts for bulging outward of annular portions 149A, 149B of a membrane 140 of the cassette 112, which may occur when the patient is positioned above the PD cycler 102 and the pistons 133A, 133B are being retracted to draw liquid into the pump chamber 138A, 138B from the patient. The corrected volume also accounts for bulging inward of the annular portions 149A, 149B of the membrane 140 of the cassette 112, which may occur when the patient is positioned below the PD cycler 102 and the pistons 133A, 133B are being advanced to force liquid from the pump chamber 138A, 138B into the patient. By accounting for bulging of the membrane, the PD system 100 can provide greater volumetric pumping accuracy, as will be discussed below.

Figure 4:
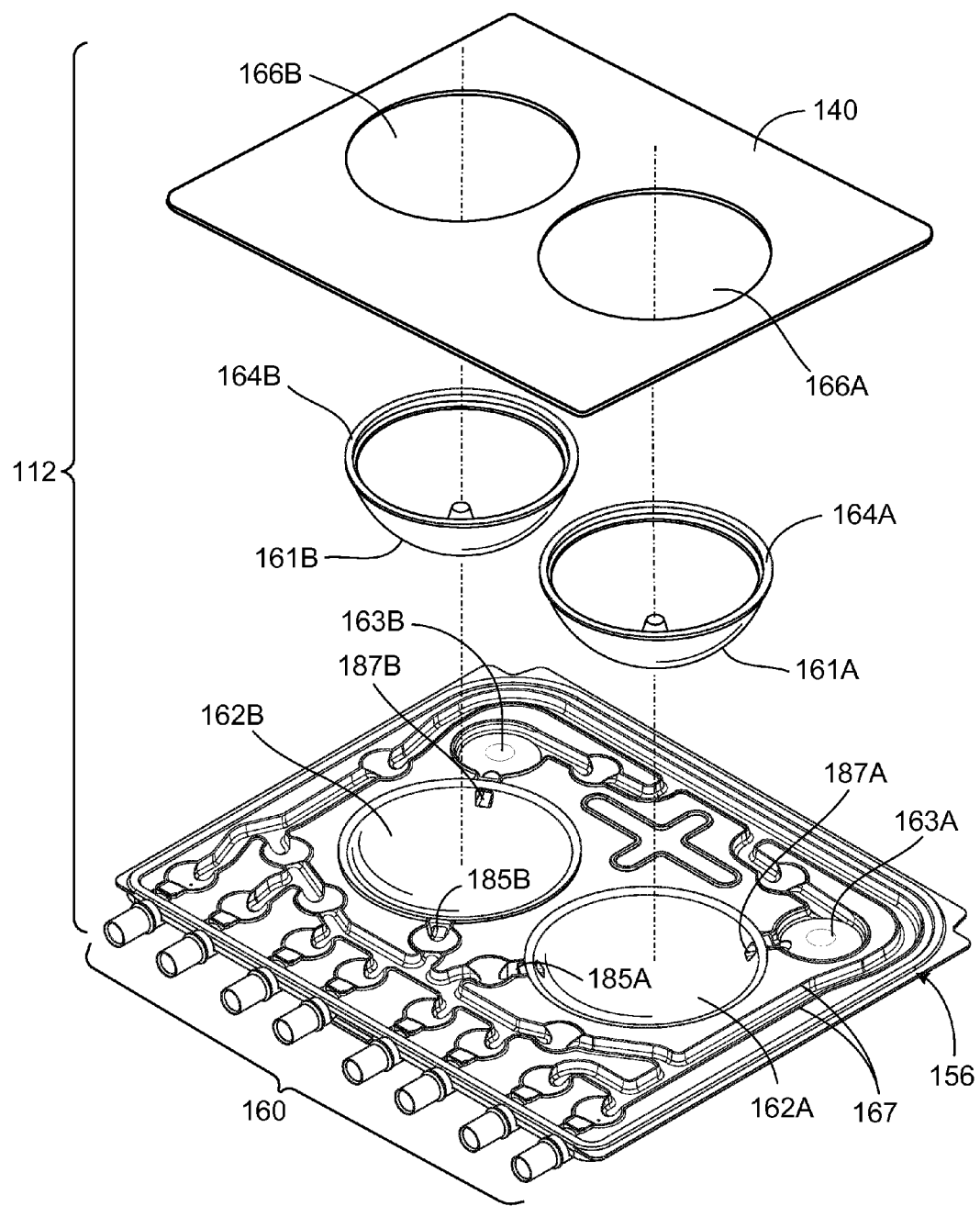
FIG. 4 is an exploded, perspective view of the PD cassette of FIG. 2, which includes dome-shaped fastening members that can be mechanically connected to the piston heads of the PD cycler of FIG. 1.
Figure 5:
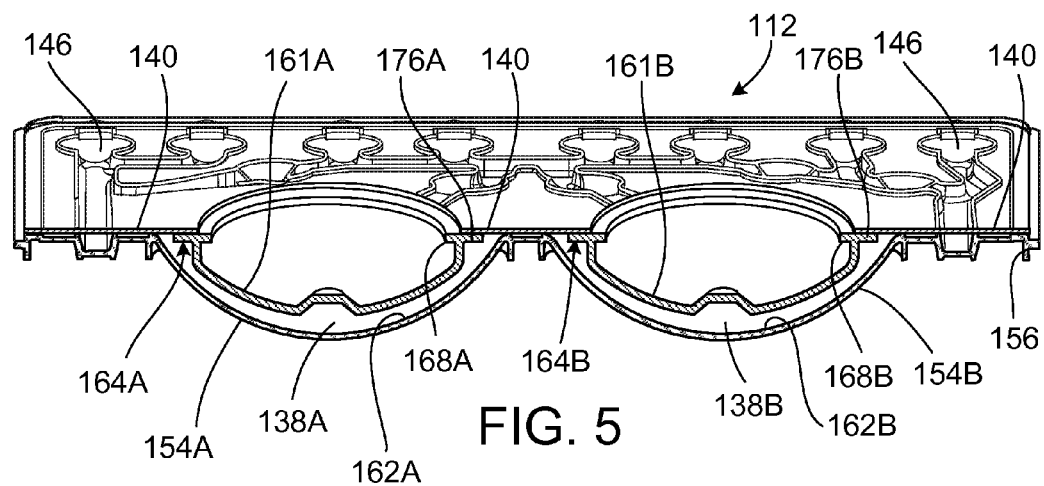
FIG. 5 is a perspective, cross-sectional view of the fully assembled PD cassette of FIG. 4.
Figure 6:
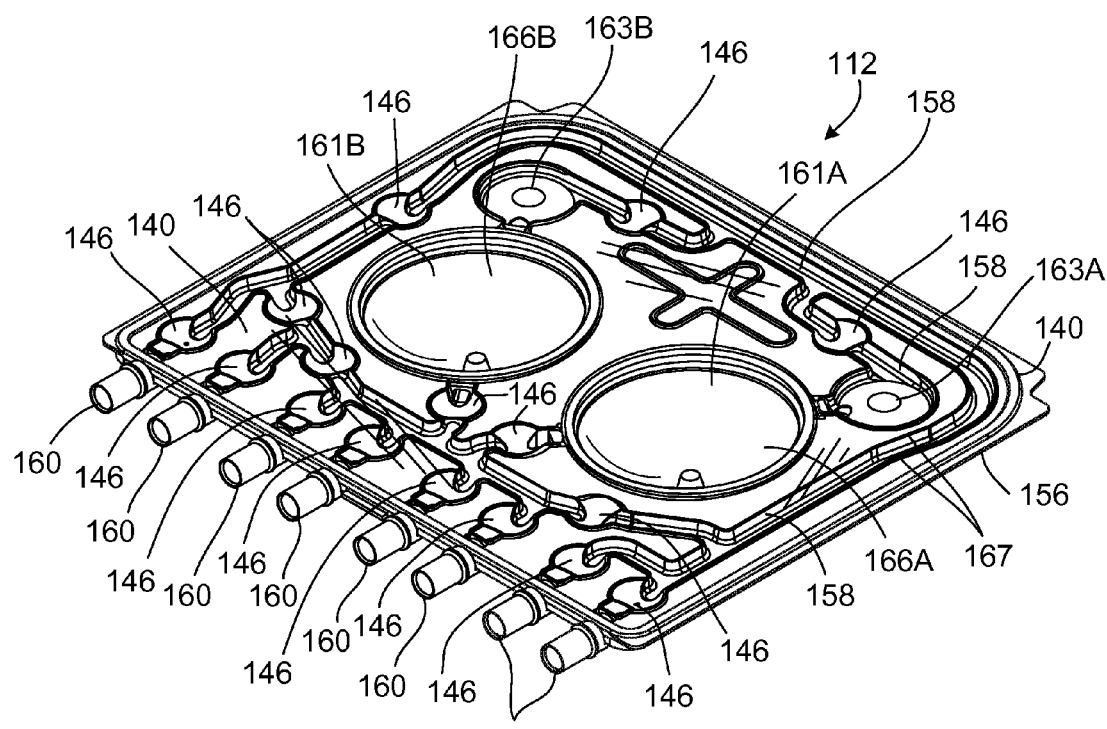
FIG. 6 is a perspective view of the fully assembled PD cassette of FIG. 4, from a flexible membrane and dome-shaped fastening member side of the PD cassette.
Figure 7:
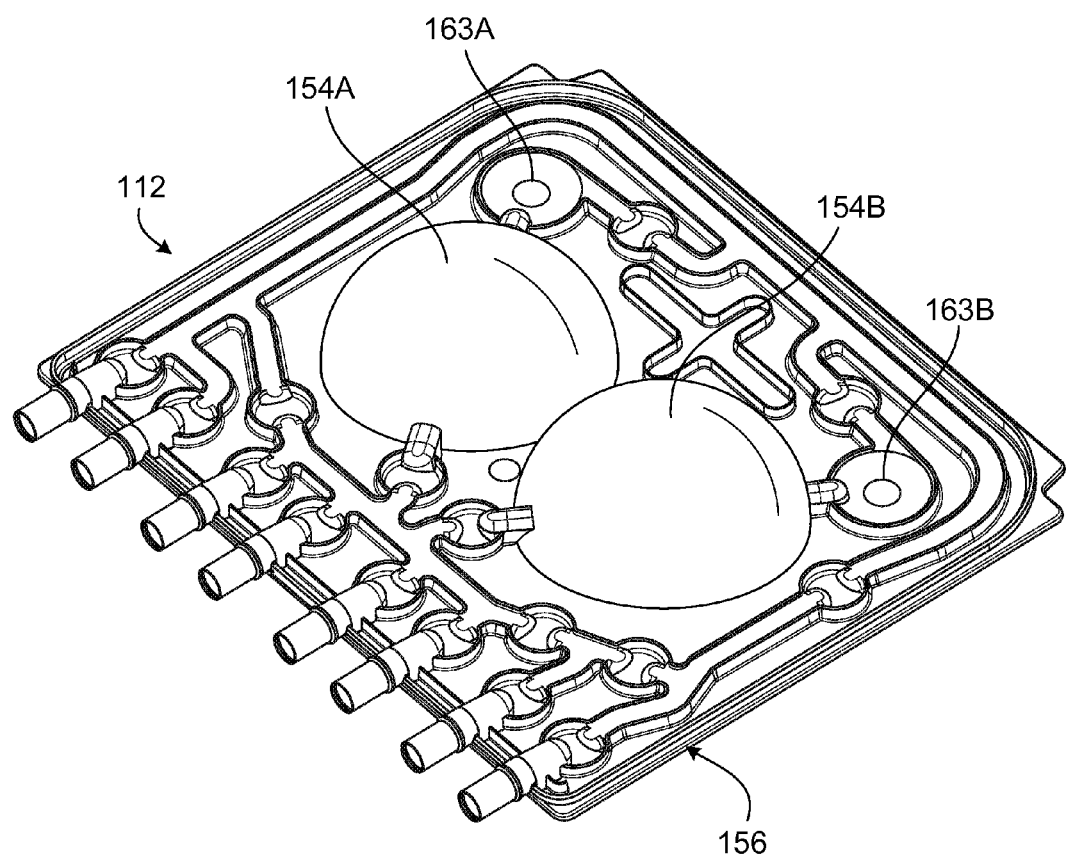
FIG. 7 is a perspective view of the fully assembled PD cassette of FIG. 4, from a rigid base side of the PD cassette.

FIG. 4 is an exploded, perspective view of the cassette 112, FIG. 5 is a perspective, cross-sectional view of the fully assembled cassette 112, and FIGS. 6 and 7 are perspective views of the assembled cassette 112, from the membrane side and from the rigid base side, respectively. Referring to FIGS. 4-6, the flexible membrane 140 of the cassette 112 is attached to a periphery of the tray-like rigid base 156. Rigid dome-shaped fastening members 161A, 161B are positioned within recessed regions 162A, 162B of the base 156. The dome-shaped members 161A, 161B are sized and shaped to receive the piston heads 134A, 134B of the PD cycler 102. In certain implementations, the dome-shaped members 161A, 161B have a diameter, measured from the outer edges of flanges 164A, 164B, of about 1.5 inches to about 2.5 inches (e.g., about 2.0 inches) and take up about two-thirds to about three-fourths of the area of the recessed regions 162A, 162B. The annular flanges 164A, 164B of the rigid dome-shaped members 161A, 161B are attached in a liquid-tight manner to portions of the inner surface of the membrane 140 surrounding substantially circular apertures 166A, 166B formed in the membrane 140. The annular flanges 164A, 164B of the rigid dome-shaped members 161A, 161B can, for example, be thermally bonded or adhesively bonded to the membrane 140. The apertures 166A, 166B of the membrane 140 expose the rigid dome-shaped members 161A, 161B such that the piston heads 134A, 134B are able to directly contact and mechanically connect to the dome-shaped members 161A, 161B during use.

The annular flanges 164A, 164B of the dome-shaped members 161A, 161B, as shown in FIG. 5, form annular projections 168A, 168B that extend radially inward and annular projections 176A, 176B that extend radially outward from the side walls of the dome-shaped members 161A, 161B. When the piston heads 134A, 134B are mechanically connected to the dome-shaped members 161A, 161B, the radially inward projections 168A, 168B engage the rear angled surfaces of the sliding latches 145A, 147A of the piston heads 134A, 134B to firmly secure the dome-shaped members 161A, 161B to the piston heads 134A, 134B. Because the membrane 140 is attached to the dome-shaped members 161A, 161B, movement of the dome-shaped members 161A, 161B into and out of the recessed regions 162A, 162B of the base 156 (e.g., due to reciprocating motion of the pistons 133A, 133B) causes the flexible membrane 140 to similarly be moved into and out of the recessed regions 162A, 162B of the base 156. This movement allows fluid to be forced out of and drawn into the fluid pump chambers 138A, 138B, which are formed between the recessed regions 162A, 162B of the base 156 and the portions of the dome-shaped members 161A, 161B and membrane 140 that overlie those recessed regions 162A, 162B.

As shown in FIGS. 5 and 6, the annular portions 149A, 149B of the membrane 140 overlie the recessed regions 162A, 162B of the base 156 of the cassette 112 and form the pump chambers 138A, 138B along with the dome-shaped members 161A, 161B. Because the membrane 140 is flexible, positive pressure in the pump chambers 138A, 138B can cause the annular portions 149A, 149B of the membrane 140 to bulge outward away from the rigid base 156 and negative pressure in the pump chambers 138A, 138B can cause the annular portions 149A, 149B of the membrane 140 to bulge inward toward the rigid base 156. This bulging outward and inward of the annular portions 149A, 149B of the membrane 140 can lead to inaccurate pumped fluid volume calculations if not accounted for when calculating the pump fluid volume. As a result of such inaccurate pumped fluid volume calculations, too little or too much dialysate could be delivered to and/or removed from a patient during peritoneal dialysis treatment, which could lead to inefficient treatment and patient discomfort. Methods described herein use a correction factor to account for bulging of the annular portions 149A, 149B of the membrane 140 during use. Thus, methods described herein can provide more accurate pumped fluid volume calculations, which can help to ensure that a desired volume of dialysate is delivered to and removed from the patient during treatment.

Referring to FIGS. 4 and 6, raised ridges 167 extend from the substantially planar surface of the base 156 towards and into contact with the inner surface of the flexible membrane 140 when the cassette 112 is compressed between the door 108 and the cassette interface 110 of the PD cycler 102 to form a series of fluid passageways 158 and to form the multiple, depressible dome regions 146, which are widened portions (e.g., substantially circular widened portions) of the fluid pathways 158, as shown in FIG. 6. The fluid passageways 158 fluidly connect the fluid line connectors 160 of the cassette 112, which act as inlet/outlet ports of the cassette 112, to the fluid pump chambers 138A, 138B. As noted above, the various inflatable valve members 142 of the PD cycler 102 act on the cassette 112 during use. During use, the dialysate flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, the flow of dialysate through the cassette 112 can be controlled through the selective depression of the depressible dome regions 146 by selectively inflating the inflatable members 142 of the PD cycler 102.

Still referring to FIGS. 4 and 6, the fluid line connectors 160 are positioned along the bottom edge of the cassette 112. As noted above, the fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysate bag lines 126, the heater bag line 128, the patient line 130, and the drain line 132. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette, as shown in FIGS. 1 and 2, the connectors 160 allow dialysate to flow into and out of the cassette 112 during use. As the pistons 133A, 133B are reciprocated, the inflatable members 142 can be selectively inflated to allow fluid to flow from any of the lines 126, 128, 130, and 132 to any of ports 185A, 185B, 187A, and 187B of the pump chambers 138A, 138B, and vice versa.

The rigidity of the base 156 helps to hold the cassette 112 in place within the cassette compartment 114 of the PD cycler 102 and to prevent the base 156 from flexing and deforming in response to forces applied to the projections 154A, 154B by the dome-shaped members 161A, 161B and in response to forces applied to the planar surface of the base 156 by the inflatable members 142. The dome-shaped members 161A, 161B are also sufficiently rigid that they do not deform as a result of usual pressures that occur in the pump chambers 138A, 138B during the fluid pumping process. Thus, the deformation or bulging of the annular portions 149A, 149B of the membrane 140 can be assumed to be the only factor other than the movement of the pistons 133A, 133B that affects the volume of the pump chambers 138A, 138B during the pumping process.

The base 156 and the dome-shaped members 161A, 161B of the cassette 112 can be formed of any of various relatively rigid materials. In some implementations, these components of the cassette 112 are formed of one or more polymers, such as polypropylene, polyvinyl chloride, polycarbonate, polysulfone, and other medical grade plastic materials. In certain implementations, these components can be formed of one or more metals or alloys, such as stainless steel. These components of can alternatively be formed of various different combinations of the above-noted polymers and metals. These components of the cassette 112 can be formed using any of various different techniques, including machining, molding, and casting techniques.

As noted above, the membrane 140 is attached to the periphery of the base 156 and to the annular flanges 164A, 164B of the dome-shaped members 161A, 161B. The portion of the membrane 140 overlying the remaining portions of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156 and to the dome-shaped members 161A, 161B. The thickness and material(s) of the membrane 140 are selected so that the membrane 140 has sufficient flexibility to flex toward the base 156 in response to the force applied to the membrane 140 by the inflatable members 142. In certain implementations, the membrane 140 is about 0.100 micron to about 0.150 micron in thickness. However, various other thicknesses may be sufficient depending on the type of material used to form the membrane 140.

Any of various different materials that permit the membrane 140 to deflect in response to movement of the inflatable members 142 without tearing can be used to form the membrane 140. In some implementations, the membrane 140 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane can alternatively include more or fewer layers and/or can be formed of different materials.

Figure 8:
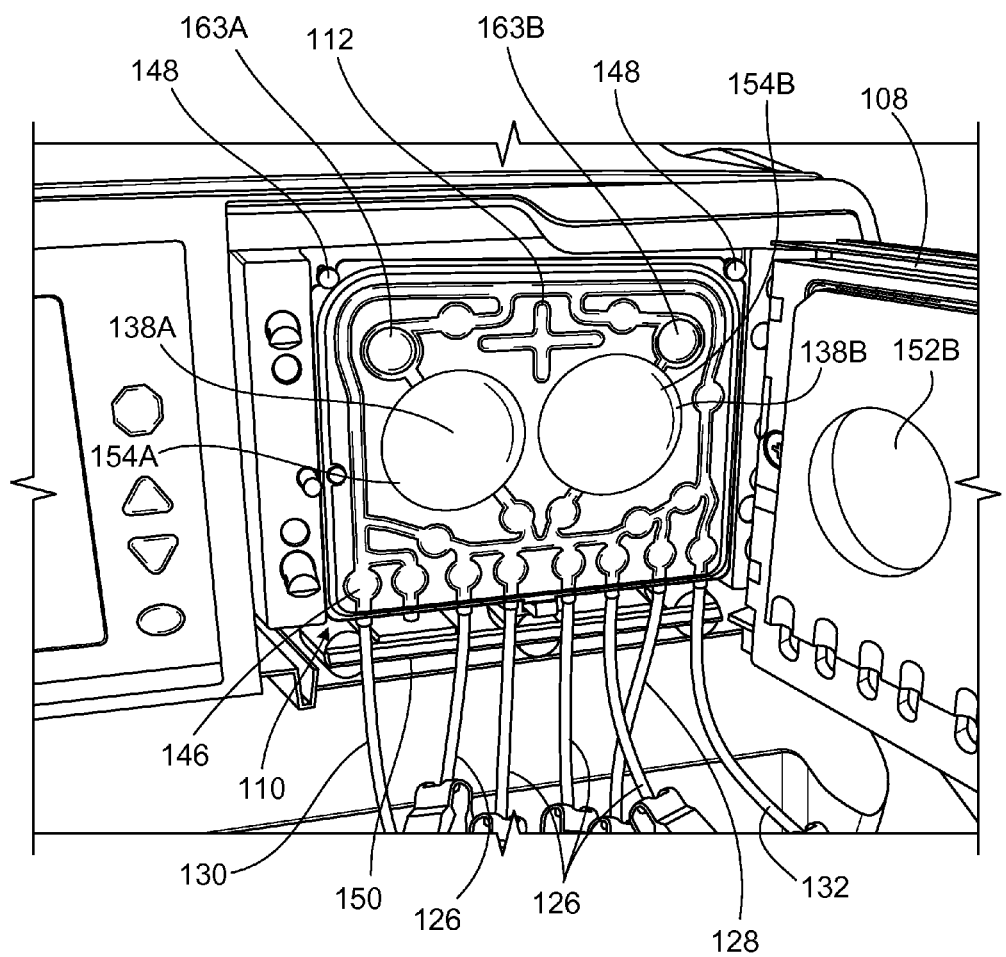
FIG. 8 is a perspective view of the PD cassette in the cassette compartment of the PD cycler of the PD system of FIG. 1.

As shown in FIG. 8, before treatment, the door 108 of the PD cycler 102 is opened to expose the cassette interface 110, and the cassette 112 is positioned with its dome-shaped members 161A, 161B aligned with the pistons 133A, 133B of the PD cycler 102, its pressure sensing chambers 163A, 163B aligned with the pressure sensors 151A, 151B of the PD cycler, its depressible dome regions 146 aligned with the inflatable members 142 of the PD cycler 102, and its membrane 140 adjacent to the cassette interface 110. In order to ensure that the cassette 112 is properly positioned on the cassette interface 110, the cassette 112 is positioned between the locating pins 148 and the spring loaded latch 150 extending from the cassette interface 110. The asymmetrically positioned connectors 160 of the cassette act as a keying feature that reduces the likelihood that the cassette 112 will be installed with the membrane 140 and dome-shaped members 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward toward the door 108. The pistons 133A, 133B are typically retracted into the piston access ports 136A, 136B during installation of the cassette 112 to avoid interference between pistons 133A, 133B and the dome-shaped members 161A, 161B and thus increase the ease with which the cassette 112 can be positioned within the cassette compartment 114.

After positioning the cassette 112 as desired on the cassette interface 110, the door 108 is closed and the inflatable pad within the door 108 is inflated to compress the cassette 112 between the inflatable pad and the cassette interface 110. This compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146 (shown in FIG. 6). Referring briefly also to FIGS. 1 and 2, the drain line 132 is then connected to a drain or drain receptacle, the heater bag line 128 is connected to the heater bag 124, and the dialysate bag lines 126 are connected to the dialysate bags 122.

The pistons 133A, 133B are then coupled to the dome-shaped members 161A, 161B of the cassette 112 and the cassette 112 and the various lines connected thereto are primed in the manner described below. After priming is complete, the patient line 130 is connected to the patient's peritoneal cavity via a catheter and treatment is carried out. Typically, the treatment begins by draining spent dialysate that was left in the patient's peritoneal cavity from the previous treatment. Fresh dialysate is then delivered to the patient's peritoneal cavity where it is allowed to dwell for a desired period of time and is then drained. This fill-dwell-drain process is typically repeated several times before the treatment is concluded.

FIGS. 9A-9G, which will be discussed below, are cross-sectional views of the system during different stages of the setup and treatment. These figures focus on the interaction between the piston 133A of the PD cycler 102 and the pump chamber 138A of the cassette 112 during treatment. The interaction between the other piston 133B and pump chamber 138B is identical and thus will not be separately described in detail.

Figure 9A:
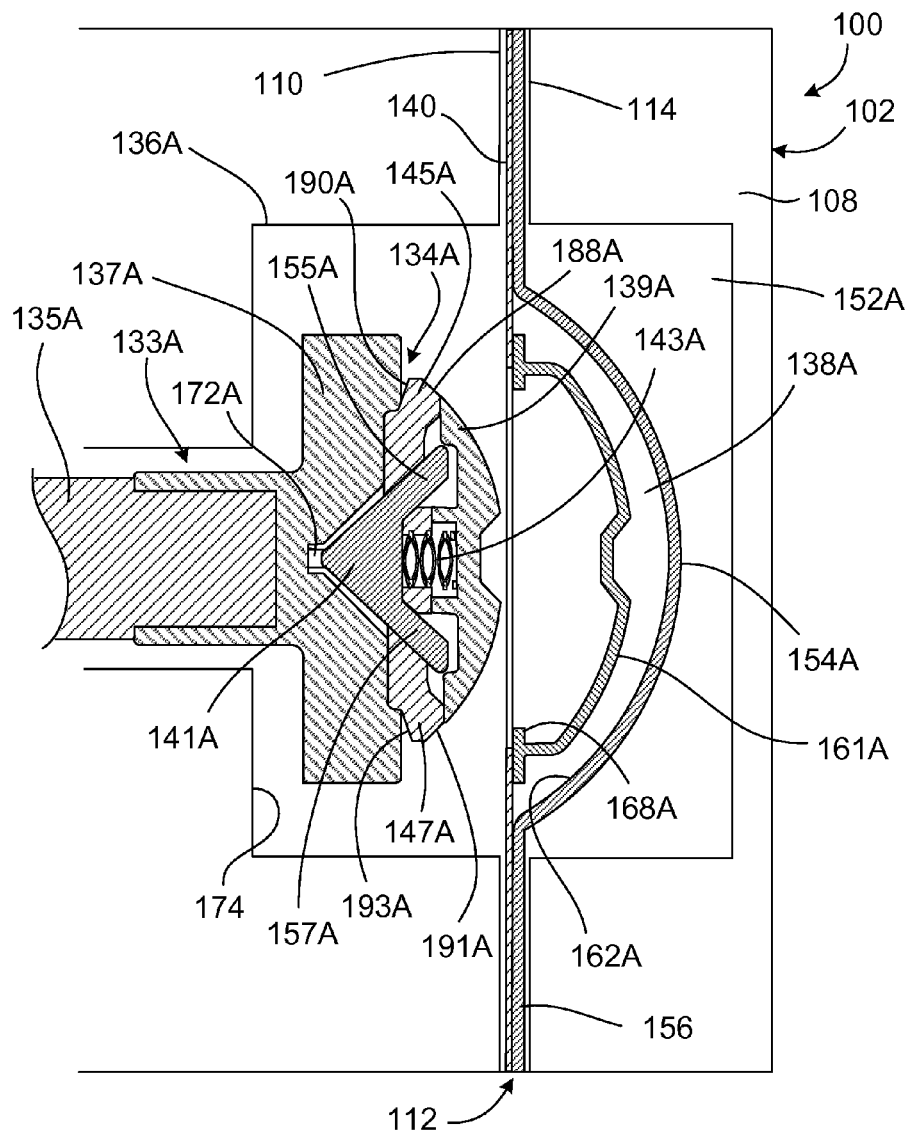
FIGS. 9A-9G are diagrammatic cross-sectional views of the PD system of FIG. 1 with the PD cassette disposed in the cassette compartment of the PD cycler, during different phases of a PD treatment.

FIG. 9A shows the piston 133A fully retracted into the piston access port 136A of the cassette interface 110. The cassette 112 is positioned in the cassette compartment 114 of the PD cycler 102 and the inflatable pad in the door 108 of the PD cycler 102 is inflated such that the cassette 112 is pressed tightly against the cassette interface 110 of the PD cycler 102, as explained above.

Figure 9B:
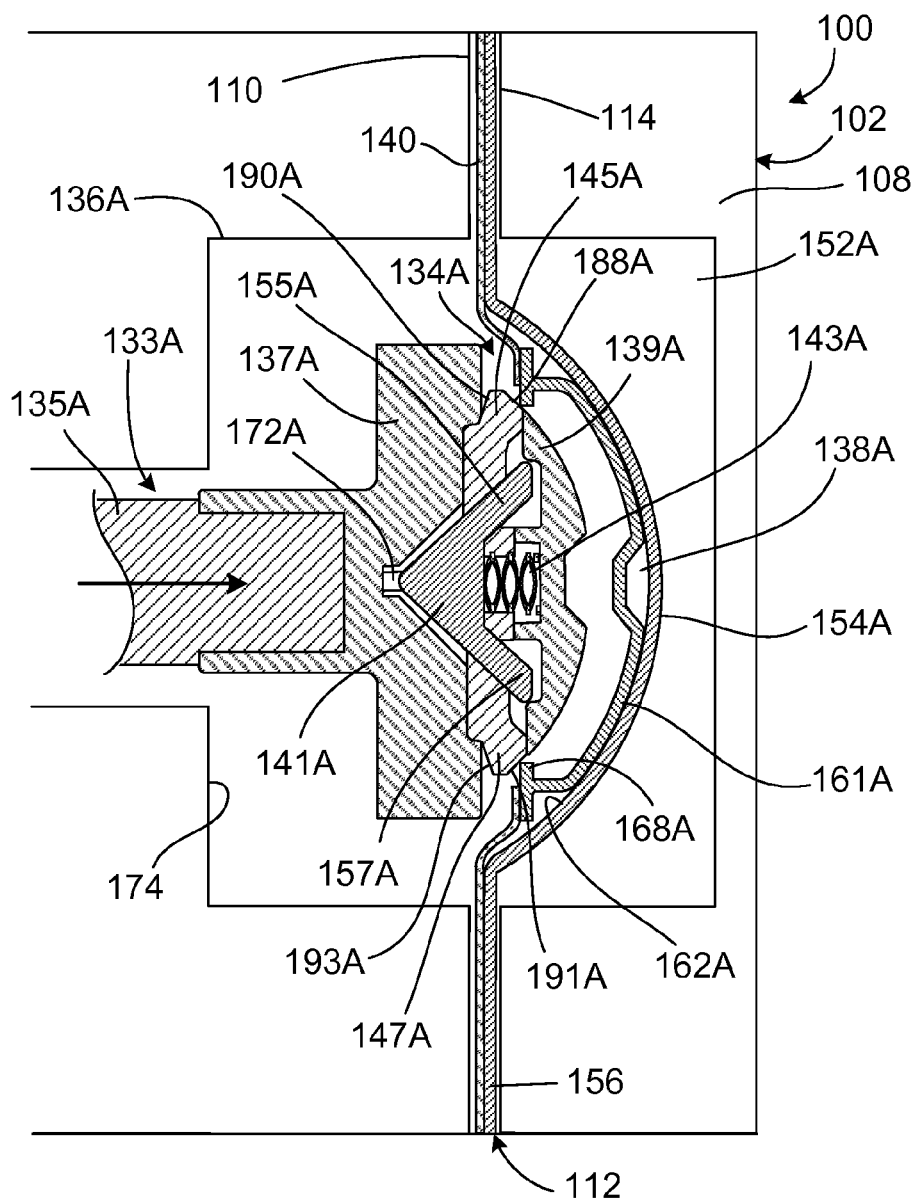

Referring to FIG. 9B, with the cassette 112 properly installed within the cassette compartment 114 of the PD cycler 102 and the appropriate line connections made, the piston 133A is advanced to initiate the process of mechanically connecting the piston head 134A of the PD cycler 102 to the dome-shaped member 161A of the cassette 112. As the piston 133A is advanced, a front angled surface 188A of a sliding latch 145A and a front angled surface 191A of a sliding latch 147A contact a rear surface of the annular projection 168A, which extends radially inward from the dome-shaped member 161A. The rear surface of the annular projection 168A is approximately perpendicular to the longitudinal axis of the piston 133A.

As the piston 133A continues to advance, the dome-shaped member 161A contacts the inner surface of the portion of the rigid base 156 that forms the recessed region 162A, as shown in FIG. 9B. The rigid base 156 prevents further forward movement of the dome-shaped member 161A. The membrane 140, which is attached to the peripheral flange 164A of the dome-shaped member 161A, also stretches and moves into the recessed region 162A due to the advancing piston 133A. Due to the angled geometries of the front angled surfaces 188A, 191A of the sliding latches 145A, 147A and the resistance provided by the rigid base 156 to the forward motion of the dome-shaped member 161A, the sliding latches 145A, 147A are caused to move radially inward (i.e., toward the longitudinal axis of the piston 133A) as the piston head 134A continues to be advanced relative to the dome-shaped member 161A. More specifically, the forward motion of the sliding latches 145A, 147A is converted into a combined forward and radially inward motion due to the sliding motion of the front angled surfaces 188A, 191A of the sliding latches 145A, 147A against the rear surface of the annular projection 168A of the dome-shaped member 161A. The radial inward movement of each of the sliding latches 145A, 147A in turn causes a forward movement of a latch lock 141A of the piston head 134A due to the mated geometries of the outer surfaces of legs 155A, 157A of the latch lock 141A and the surfaces of the sliding latches 145A, 147A that are positioned adjacent to and brought into contact with those outer surfaces of the legs 155A, 157A. This forward movement of the latch lock 141A is resisted by a spring 143A in the piston head.

Figure 9C:
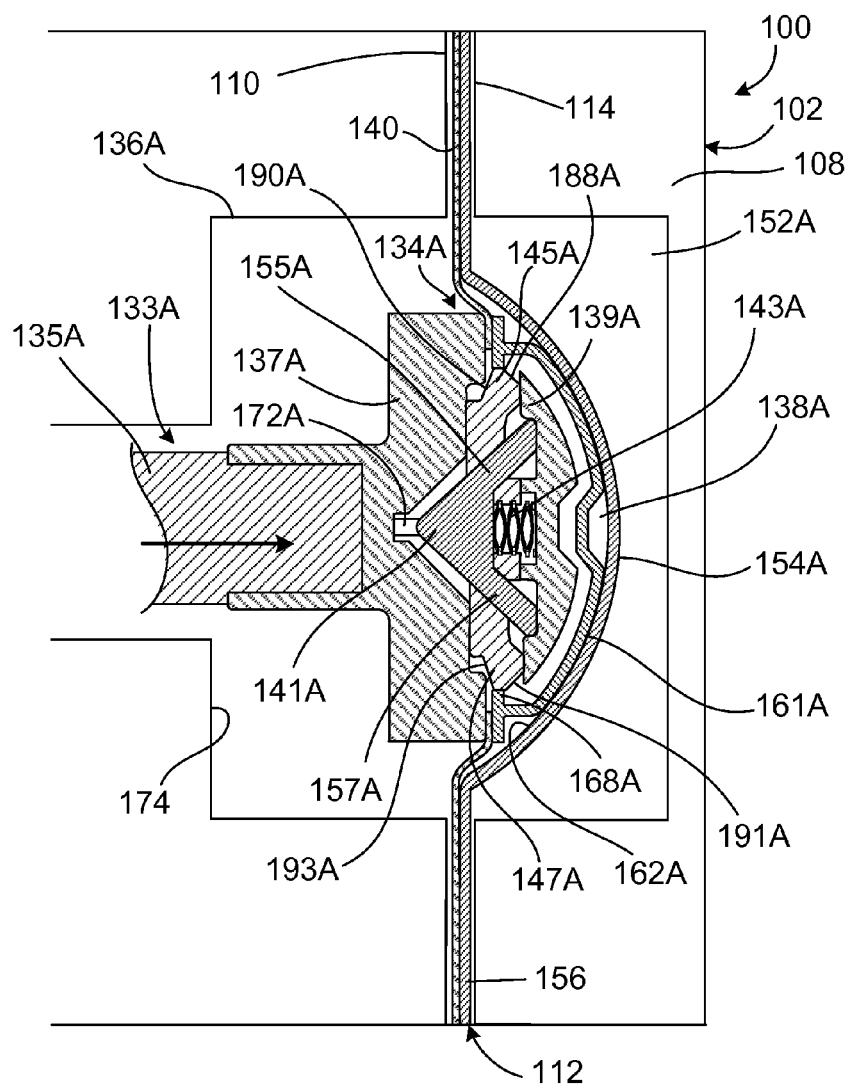

FIG. 9C shows the piston head 134A at a point during the connection process at which the sliding latches 145A, 147A have been deflected radially inward a sufficient distance to allow the sliding latches 145A, 147A to pass beyond the annular projection 168A that extends radially inward from the dome-shaped member 161A. In this position, outer peripheral surfaces of the sliding latches 145A, 147A, which are substantially parallel to the longitudinal axis of the piston 133A, contact and slide along an inner surface of the annular projection 168A of the dome-shaped member 161A, which is also substantially parallel to the longitudinal axis of the piston 133A. The spring 143A is further compressed due to the radially inwardly deflected positions of the sliding latches 145A, 147A.

Figure 9D:
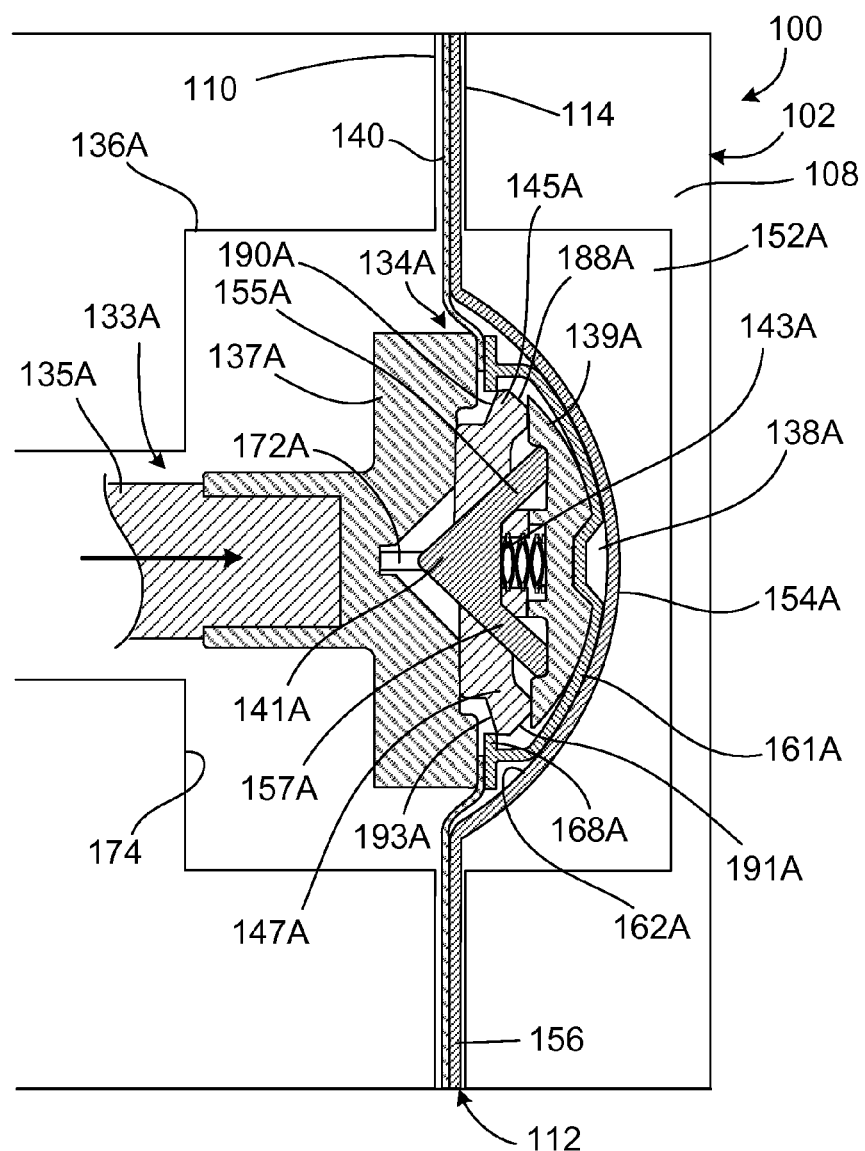

Referring to FIG. 9D, as the sliding latches 145A, 147A pass beyond the annular projection 168A, the spring 143A is allowed to expand. The expansion of the spring 143A causes the latch lock 141A to move rearward. As a result, the outer surfaces of the legs 155A, 157A of the latch lock 141A contact the correspondingly angled adjacent surfaces of the sliding latches 145A, 147A, causing the sliding latches 145A, 147A to move radially outward underneath the projection 168A of the dome-shaped member 161A. Rear angled surfaces 190A, 193A of the sliding latches 145A, 147A ride along the front surface of the projection 168A of the dome-shaped member 161A, which is slightly angled toward the rear of the dome-shaped member 161A, as the sliding latches 145A, 147A move radially outward. The sliding latches 145A, 147A become wedged beneath the projection 168A as the sliding latches 145A, 147A move radially outward.

Figure 9E:
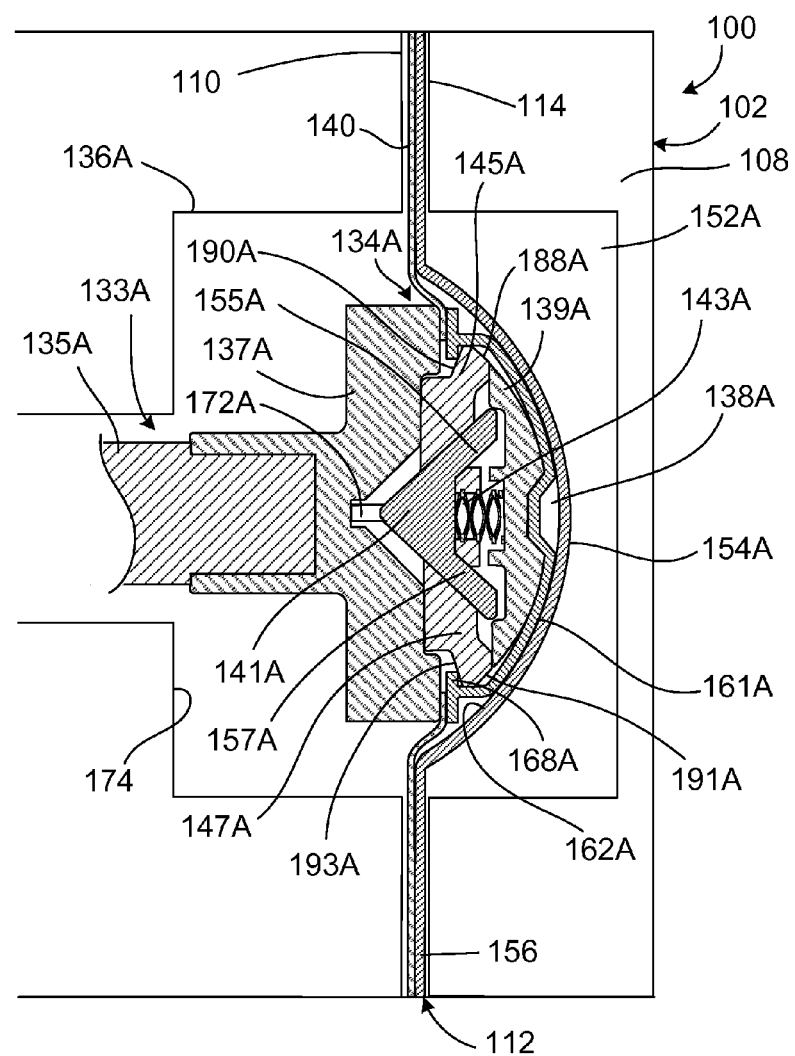

FIG. 9E illustrates the completed mechanical connection between the piston head 134A and the dome-shaped member 161A in which the sliding latches 145A, 147A have moved to maximum outwardly displaced positions within the dome-shaped member 161A. In this configuration, the projection 168A of the dome-shaped member 161A is effectively pinched between a rear member 137A of the piston head 134A and the sliding latches 145A, 147A, resulting in a secure engagement between the piston head 134A and the dome-shaped member 161A. As a result of the secure engagement of the piston head 134A to the dome-shaped member 161A, the amount of slippage of the piston head 134A relative to the dome-shaped member 161A can be reduced (e.g., minimized) and thus precise pumping can be achieved.

After mechanically coupling the piston head 134A of the PD cycler 102 to the dome-shaped member 161A of the cassette 112, a "learning" process is carried out to ensure that the control unit 139 knows the position of the piston 133A in relation to the pump chamber 138A of the cassette 112 and can be reciprocated in a manner to draw a desired amount of fluid into and pump a desired amount of fluid out of the pump chamber 138A of the cassette 112. Initially, the pistons 133A, 133B are moved to a home position which is sensed by a conventional optical sensor. The stepper motor encoder value is then set to zero. Next the pistons 133A, 133B are advanced until they contact the rigid base of the cassette 112. The control unit 139 can detect when the pistons 133A, contact the rigid base of the cassette 112 because the encoder value of the stepper motor encoder, which is connected to the control unit 139, will no longer change. The pistons 133A, 133B are then retracted slightly by moving the stepper motors a certain number of counts (e.g., 1900 counts). These are the "OUT" positions of the pistons 133A, 133B. Then, the pistons 133A, 133B are further retracted by rotating the stepper motors a desired number of additional counts (e.g., 5000 counts). These are the "IN" positions of the pistons 133A, 133B. To draw fluid into the pump chambers 138A, 138B and pump fluid out of the pump chambers 138A, 138B during priming and treatment, the pistons 133A, 133B are reciprocated between the "IN" and "OUT" positions.

After carrying out the above-noted "learning" process, the cassette 112 and the various lines connected thereto are primed. To prime the cassette 112 and the various lines, the pistons 133A and the inflatable members 142 are operated to pump dialysate from the heater bag 124 to the drain and from each of the dialysate bags 122 to the drain to force any air trapped in the heater bag line 128 and the dialysate bag lines 126 to the drain. Dialysate is also passed (e.g., by gravity) from the heater bag 124 to the patient line 130 to force any air trapped in the patient line out of a hydrophobic filter positioned at the distal end of the patient line 130.

Figure 9F:
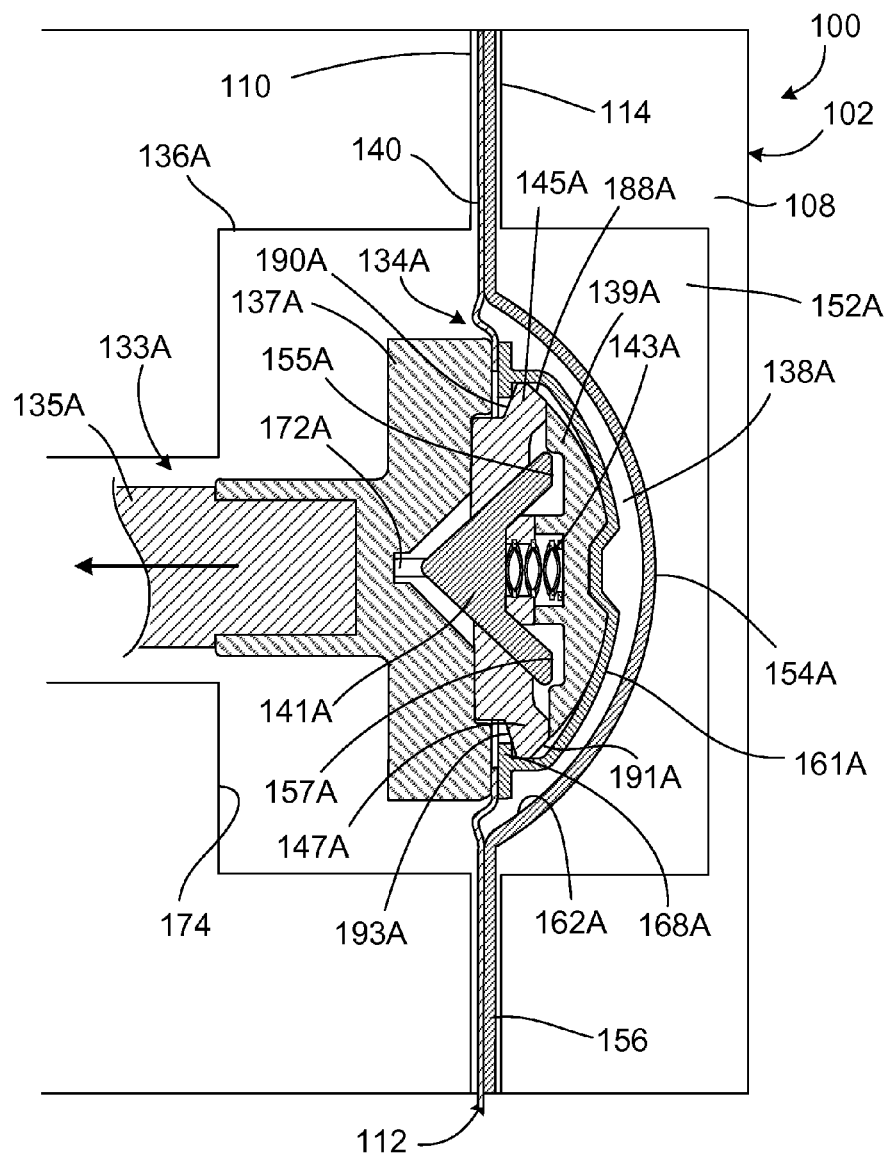

After priming is complete, the patient line 130 is connected to the peritoneal cavity of the patient and the PD cycler 102 is operated to drain any spent dialysate that was left in the patient's peritoneal cavity from a previous treatment. To drain the spent dialysate from the patient's peritoneal cavity, the inflatable members 142 of the PD cycler 102 are configured to create an open fluid flow path between the patient line 130 and the port 187A (shown in FIG. 4) of the pump chamber 138A, and the piston 133A is retracted to draw spent dialysate from the peritoneal cavity of the patient into the pump chamber 138A via the patient line 130, as shown in FIG. 9F. Because the piston head 134A is mechanically connected to the dome-shaped member 161A and the dome-shaped member 161A is attached to the membrane 140 of the cassette 112, the retraction of the piston 133A causes the dome-shaped member 161A and the portion of the membrane 140 attached to the dome-shaped member 161A to move rearwardly. As a result, the volume of the pump chamber 138A is increased and spent dialysate is drawn into the pump chamber 138A from the peritoneal cavity of the patient. The spent dialysate travels from the patient line 130 through the pressure sensing chamber 163A and then enters the pump chamber 138A via the port 187A. The pressure sensor 151A is able to monitor the pressure in the pressure sensing chamber 163A, which is approximately equal to the pressure in the pump chamber 138A, during this process.

As shown in FIG. 9F, under certain conditions, the positive pressure generated within the pump chamber 138A as the piston 133A is retracted to draw liquid into the pump chamber 138A causes the annular portion 149A of the membrane 140 to bulge outwardly from the rigid base 156 of the cassette 112 and thus increases the total volume of the pump chamber 138A. For example, when the patient is positioned above the PD cycler 102 and the piston 133A is retracted to draw spent dialysate from the patient into the pump chamber 138A, gravity will assist the transfer of the spent dialysate from the patient to the pump chamber 138A, resulting in a greater pressure within the pump chamber 138A. This increased pressure within the pump chamber 138A can cause the annular portion 149A of the membrane 140 to bulge outwardly. If unaccounted for, this bulging of the annular portion 149A of the membrane 140 can lead to greater than a desired volume of spent dialysate being removed from the patient or can lead to the PD system 100 operating to drain fluid from the patient after the patient has been emptied and thus unnecessarily prolong the treatment.

To ensure that the desired volume of dialysate is drawn from the patient during treatment, the theoretical volume of dialysate that is drawn into the pump chamber 138A from the peritoneal cavity of the patient is first calculated by the control unit 139 and stored in memory of the control unit 139. The theoretical volume of dialysate drawn into the pump chamber 138A is determined using the following equation:

$$V_{dialysate} = V_{total} - V_{air}, \quad (1)$$

where $V_{dialysate}$ is the volume of dialysate in the pump chamber;
$V_{total}$ is the total pump chamber volume, and
$V_{air}$ is the volume of air in the pump chamber.

The total pump chamber volume ($V_{total}$) can be determined based on the position of the piston 133A. Specifically, since the volume of the pump chamber (prior to the cassette membrane being deformed by the piston 133A) is known based on the dimensions of the cassette and the volume of the piston head 134A is known based on the dimensions of the piston head 134A, the total volume of the pump chamber (i.e., the total volume of the pump chamber when the piston 133A is in the retracted position or "IN" position) can be determined by subtracting the volume of the portion of the piston head 134A that projects into the pump chamber in the "IN" position from the pump chamber volume when the membrane 140 is undeformed. The volume of the portion of the piston head 134A that penetrates into the volume of the pump chamber in the "IN" position can be determined based on the linear position of the piston 133A relative to the cassette 112.

As an alternative to performing the above-noted calculations to determine the total pump chamber volume ($V_{total}$), it is possible to determine this volume empirically. For example, the cassette 112 can be positioned in the cassette compartment 114 of the PD cycler 102 and the piston 133A can be retracted a certain distance to draw dialysate into the pump chamber 138A. The piston 133A is then advanced to pump the dialysate from the pump chamber 138A to a collection bag sitting on a weight scale that is level with the PD cycler 102. The volume of dialysate pumped to the collection bag can then be determined based on the weight of the dialysate. In addition, the distance by which the piston 133A was retracted is known. Thus, the retracted position of the piston 133A and the total volume of fluid contained in the pump chamber 138A that corresponds to that retracted piston position are known and can be stored in a look-up table accessible by the control unit of the PD cycler 102. This process can be repeated many times to arrive at an accurate correlation between the retracted piston position and the total volume of the pump chamber 138A when the piston 133A is in that retracted position.

After determining the retracted position of the piston 133A and the total pump chamber volume ($V_{total}$), the volume of air in the pump chamber ($V_{air}$) is determined using the following equation:

$$V_{air} = ((Vol_{25\ mbar} - Vol_{300\ mbar}) * slope + intercept)/1000 \quad (2)$$

where $Vol_{25\ mbar}$ is the volume of the pump chamber when the pump chamber 138A is isolated and the pressure sensor 151A detects a pressure of 25 mbar;

$Vol_{300\ mbar}$ is the volume of the pump chamber when the pump chamber 138A is isolated and the pressure sensor 151A detects a pressure of 300 mbar;

$$slope = (7*1000000)/1704; \text{ and}$$

$$intercept = -slope*200.$$

The respective volumes of the pump chamber 138A when the pressure sensor 151A detects pressures of 25 mbar and 300 mbar can be determined based on the position of the piston 133A when those pressures are detected. As discussed above, due to the known geometries of the piston head 134A and the pump chamber 138A (when the membrane 140 is undeformed), the control unit 139, which receives data from the pressure sensor 151A and from the stepper motor encoder, can use the known position of the piston 133A when the pressure sensor 151A detects pressures of 25 mbar and 300 mbar to mathematically determine the volumes of the pump chamber 138A at those pressures. Alternatively, the control unit 139 can access a look-up table that contains various piston positions and corresponding pump chamber volumes. The look-up table could be populated by first mathematically calculating the pump chamber volume associated with each piston position or by empirically determining the pump chamber volume associated with each piston position in the manner described above.

After determining the total volume ($V_{total}$) of the pump chamber 138A (assuming no bulging of the cassette membrane 140) and the volume of air in the pump chamber 138 ($V_{air}$), the volume of dialysate in the pump chamber 138 ($V_{dialysate}$) determined using equation 1 above (i.e., by subtracting the volume of air in the pump chamber 138A from the total volume of the pump chamber 138A).

The volume of dialysate determined to be in the pump chamber 138 ($V_{dialysate}$) using equation 1 above will differ from the actual volume of dialysate in the pump chamber 138A if the annular portion 149A of the cassette membrane 140 bulges outward as a result of high positive pressure within the pump chamber 138A when the piston 133A is retracted. The tendency of the annular portion 149A of the membrane 140 to bulge outward during retraction of the piston 133A is closely correlated with the pressure within the pump chamber 138A or the sensing chamber 163A adjacent the pump chamber 138A when the piston 133A is in the retracted position (i.e., at the end of the inward stroke). For example, when the patient is positioned above the PD cycler 102 during the drain cycle, gravity assists the pumping operation to facilitate the transfer of spent dialysate from the patient to the pump chamber 138A. As a result, increased positive pressure is generated within the pump chamber 138A. It is this increase in pressure that causes the annular portion 149A of the cassette membrane 140 to bulge outward.

At the end of each inward stroke of the piston 133A during the drain phase of the cycle, the pump chamber 138A is isolated by inflating the inflatable member 142 that is positioned adjacent the pressure sensing chamber 163A of the cassette 112 (i.e., near the top of the pump chamber 138A) and by inflating the inflatable member 142 that is adjacent the inlet/outlet port positioned near the bottom of the pump chamber 138A. After the pump chamber 138A has been isolated in this manner for a certain period of time (e.g., 0.5 seconds), a signal indicating the pressure within the sensing chamber 163A, which is approximately equal to the pressure within the pump chamber 138A, is transmitted from the pressure sensor 151A to the control unit 139. Using the rules and equations below, the control unit 139 determines an appropriate correction factor (K) to be used based on the measured pressure:

If $P \leq 30$ mbar, then $K=0$;

If $P \geq 80$ mbar, then $K=0.02$; and

If 30 mbar$<P<80$ mbar, then $K=((P-30)*2/5)/1000$, where P is the pressure reading of the pressure sensor 151A when the pump chamber 138A is isolated at the end of the inward piston stroke.

After determining the appropriate correction factor (K), the control unit 139 uses that correction factor (K) to determine an adjustment volume ($V_{adjustment}$), as follows:

$$V_{adjustment} = V_{dialysate} * K, \quad (3)$$

where $V_{dialysate}$ is the volume of dialysate previously determined to be in the pump chamber 138 and K is the correction factor selected by the control unit 139 using the rules set forth above.

The control unit 139 then uses the calculated adjustment volume ($V_{adjustment}$) to adjust the volume of dialysate previously determined to be in the pump chamber 138 ($V_{dialysate}$) to determine a corrected volume of dialysate in the pump chamber 138 ($V_{corrected}$), as follows:

$$V_{corrected} = V_{dialysate} + V_{adjustment} \quad (4)$$

Figure 9G:
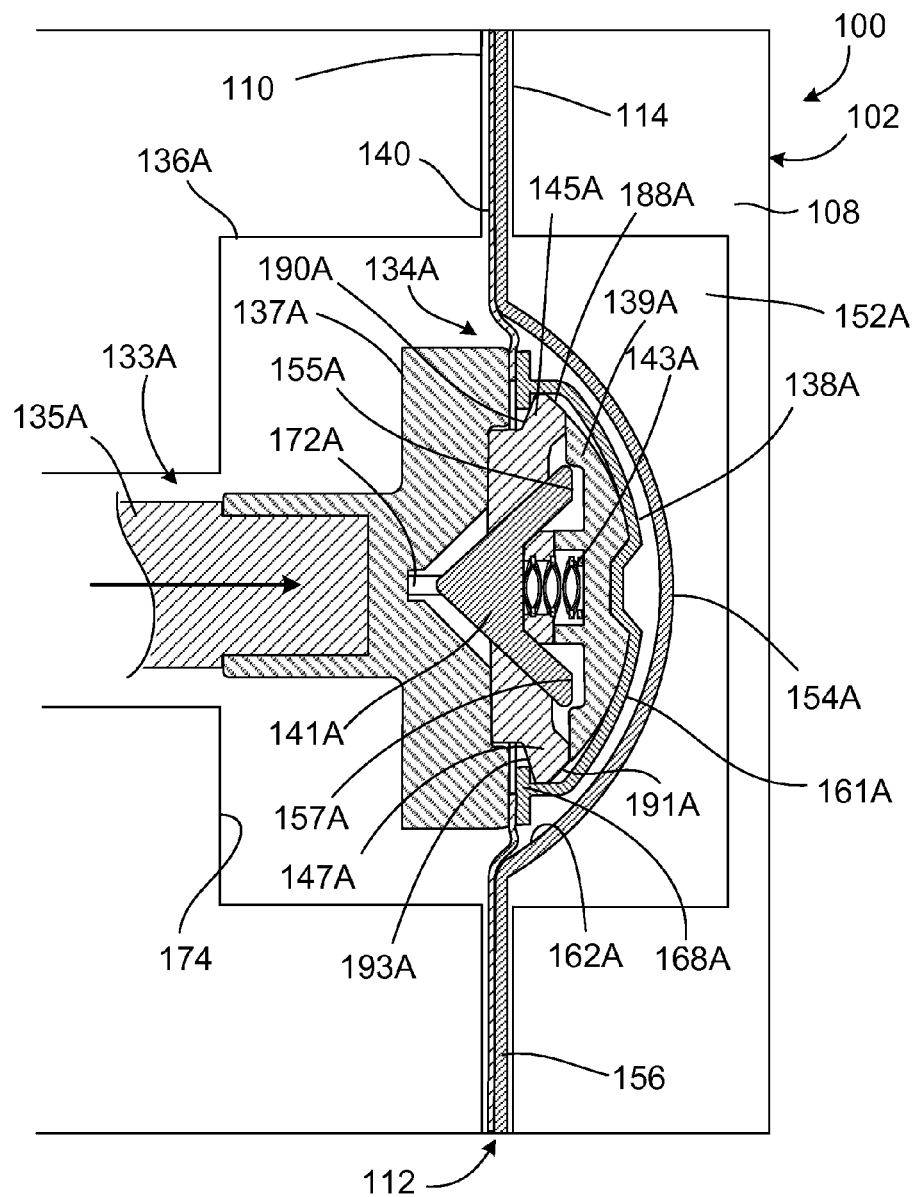

Referring to FIG. 9G, after drawing the dialysate into the pump chamber 138A from the peritoneal cavity of the patient, the inflatable members 142 are configured to create an open fluid flow path between the port 185A (shown in FIG. 4) of the pump chamber 138A and the drain line 132, and the dialysate is forced out of the pump chamber 138A to the drain by advancing the piston 133A and decreasing the volume of the pump chamber 138A. The piston 133A is typically advanced until the dome-shaped member 161A contacts or nearly contacts the inner surface of the recessed region of the base 156 so that substantially all of the dialysate is forced out of the fluid pump chamber 138A via the port 185A.

During the patient drain phase of the treatment, the pistons 133A, 133B are typically alternately operated such that the piston 133A is retracted to draw spent dialysate solution into the pump chamber 138A from the patient while the piston 133B is advanced to pump spent dialysate solution from the pump chamber 138B to the drain and vice versa. The control unit 139 determines an appropriate correction factor based on pressure signals received from the pressure sensor 151B and uses that correction factor to calculate a corrected volume of spent dialysate drawn into the pump chamber 138B from the patient in the same manner as discussed above with respect to the pump chamber 138A. The control unit determines a corrected volume of fluid drawn into the pump chambers 138A, 138B from the patient for each stroke of the pistons 133A, 133B.

The corrected volume ($V_{corrected}$) for each inward piston stroke during the drain phase is stored in memory of the control unit 139. This allows the total corrected volume during the patient drain phase (i.e., the sum of corrected fluid volumes calculated for each piston stroke during the patient drain phase) to be monitored. When the total corrected volume of fluid drained from the patient during the patient drain phase reaches the total desired volume of fluid to be drained during the drain phase, the cycler 102 transitions from the patient drain phase to a patient fill phase.

To begin the patient fill phase, the inflatable members 142 are configured to create a clear fluid flow path between the pump chamber 138A and the heater bag line 128, and then the piston 133A is retracted, as shown in FIG. 9F, to draw warm dialysate from the heater bag 124 to the pump chamber 138A. The warm dialysate travels from the heater bag 124 through the heater bag line 128 and into the pump chamber 138A via the port 185A.

The warm dialysate is then delivered to the peritoneal cavity of the patient via the patient line 130 by configuring the inflatable members 142 to create a clear fluid flow path between the pump chamber 138A and the patient line 130 and advancing the piston 133A, as shown in FIG. 9G. The warm dialysate exits the pump chamber 138A via the port 187A and travels through the pressure sensing chamber 163A to the patient line 130 before reaching the peritoneal cavity of the patient. The pressure sensor 151A is able to monitor the pressure in the pressure sensing chamber 163A, which is approximately equal to the pressure in the pump chamber 138A, during this process.

Under certain conditions, the negative pressure generated within the pump chamber 138A as the piston 133A is advanced causes the annular portion 149A of the membrane 140 to bulge inwardly toward the rigid base 156 of the cassette 112, as shown in FIG. 9F, which decreases the total volume of the pump chamber 138A at the end of the piston stroke, as compared to the total volume of the pump chamber 138A when no such bulging of the membrane 140 occurs. For example, when the patient is positioned below the PD cycler 102 during the fill cycle, gravity facilitates the ease with which the warmed dialysate can be delivered to the patient. As a result, a greater negative pressure is generated in the pump chamber 138 due to the pumping action of the piston 138A and the annular portion 149A of the membrane 140 bulges inward. As a consequence of the inwardly bulging membrane 140, less fluid remains in the pump chamber at the end of the piston stroke (as compared to a situation in which no such bulging of the membrane occurs) and more fluid is delivered to the patient. If unaccounted for, this bulging of the annular portion 149A of the membrane 140 can lead to more than a desired volume of fresh dialysate being delivered to the patient, which can cause the patient discomfort and can lead to longer treatment times than are necessary. Specifically, the excess volume of fluid delivered to the patients can result in the patient being overfilled, which can cause discomfort. And, due to the additional piston strokes required to fill the patient with the excess volume of dialysate, the treatment would be unnecessarily prolonged.

To ensure that a desired volume of dialysate is delivered to the patient during the patient fill phase, the volume of dialysate that is pumped out of the pump chamber 138A is calculated by the control unit 139 for each stroke of the piston 133A. Because the starting volume of the fluid pump chamber 138A (assuming no bulging of the cassette membrane 140) and the volume of the dome-shaped member 161A are known, the linear distance traveled by the dome-shaped member 161A, which is equal to the linear distance traveled by the piston 133A, can be used to determine the volume of dialysate pumped out of the fluid pump chamber 138A. To allow this linear distance to be determined, signals indicating the number of revolutions or steps of the motor used to drive the piston 133A during use are transmitted to the control unit 139. The linear distance traveled by the piston 133A (and thus the linear distance traveled by the dome-shaped member 161A) can be determined based on the number of revolutions or steps of the motor used to drive the piston 133A. Thus, the theoretical volume of solution pumped out of the fluid pump chamber 138A can be determined based on the number of revolutions or steps of the motor (i.e., the position of the piston 133A). Equations (1) and (2) above can be used for determining the theoretical volume.

As discussed above, this theoretical volume of fluid pumped out of the pump chamber 138A will differ from the actual volume of fluid pumped out of the pump chamber 138A if the annular portion 149A of the cassette membrane 140 bulges inward as a result of excessive negative pressure generated within the pump chamber 138A when the piston 133A is advanced. It has been found that the tendency of the annular portion 149A of the membrane 140 to bulge inward during advancement of the piston 133A is closely correlated with the pressure within the pump chamber 138A and the sensing chamber 151A adjacent the pump chamber 138A. For example, when the patient is positioned below the PD cycler 102 during the fill cycle, gravity assists the pumping operation to facilitate the transfer of fresh dialysate from the pump chamber 138A to the patient. As a result, increased negative pressure is generated within the pump chamber 138A. It is this increase in negative pressure that causes the annular portion 149A of the cassette membrane 140 to bulge inward.

At the end of each outward stroke of the piston 133A (i.e., when the piston 133A is in the "OUT" position) during the fill phase of the cycle, the pump chamber 138A is isolated by inflating the inflatable member 142 that is positioned adjacent the pressure sensing chamber 163A of the cassette 112 (i.e., near the top of the pump chamber 138A) and by inflating the inflatable member 142 that is adjacent the inlet/outlet port positioned near the bottom of the pump chamber 138A. After the pump chamber 138A has been isolated in this manner for a certain period of time (e.g., 0.5 seconds), a signal indicating the pressure within the sensing chamber 163A, which is approximately equal to the pressure within the pump chamber 138A, is transmitted from the pressure sensor 151A to the control unit 139. Using the rules and equations below, the control unit 139 determines an appropriate correction factor (K) to be used based on the measured pressure:

If $P \leq -40$ mbar, then $K=0.015$;

If $P \geq 40$ mbar, then $K=0$; and

If $-40$ mbar$<P<40$ mbar, then $K=(15-(P+40)*15/80)/1000$, where P is the pressure reading of the pressure sensor 151A and K is the correction factor.

After determining the appropriate correction factor, the control unit 139 multiplies the previously determined theoretical fluid volume by the correction factor to determine an adjustment volume (see Equation (3) above) and then adds the adjustment volume to the previously determined theoretical fluid volume to arrive at the corrected volume (see Equation (4) above). The corrected fluid volume for each piston stroke is stored in memory of the control unit 139. This allows the total corrected volume during the patient fill cycle (i.e., the sum of corrected fluid volumes calculated for each piston stroke during the patient fill cycle) to be monitored.

During the patient fill phase of the treatment, the pistons 133A, 133B are typically alternately operated such that the piston 133A is retracted to draw warm dialysate into the pump chamber 138A from the heater bag 124 while the piston 133B is advanced to pump warm dialysate from the pump chamber 138B to the patient and vice versa. The control unit 139 determines an appropriate correction factor based on pressure signals received from the pressure sensor 151B and uses that correction factor to calculate a corrected volume of warm dialysate pumped out of the pump chamber 138B to the patient in the same manner as discussed above with respect to the pump chamber 138A. The control unit 139 determines a corrected volume of fluid pumped out of the pump chambers 138A, 138B to the patient for each stroke of the pistons 133A, 133B. When the total corrected volume of fluid pumped to the patient reaches the total desired volume of fluid to be pumped to the patient, the cycler 102 transitions from the patient fill phase to a dwell phase during which the dialysate is allowed to sit within the peritoneal cavity of the patient for a long period of time.

During the dwell period, toxins cross the peritoneum of the patient into the dialysate from the patient's blood. As the dialysate dwells within the patient, the PD cycler 102 prepares fresh dialysate for delivery to the patient in a subsequent cycle. In particular, the PD cycler 102 pumps fresh dialysate from one of the four full dialysate bags 122 into the heater bag 124 for heating. To do this, the pump of the PD cycler 102 is activated to cause the pistons 133A, 133B to reciprocate and certain inflatable members 142 of the PD cycler 102 are inflated to cause the dialysate to be drawn into the fluid pump chambers 138A, 138B of the cassette 112 from the selected dialysate bag 122 via its associated line 126. The dialysate is then pumped from the fluid pump chambers 138A, 138B to the heater bag 124 via the heater bag line 128.

After the dialysate has dwelled within the patient for the desired period of time, the spent dialysate is pumped from the patient to the drain in the manner described above. The heated dialysate is then pumped from the heater bag 124 to the patient where it dwells for a desired period of time. These steps are repeated with the dialysate from two of the three remaining dialysate bags 122. The dialysate from the last dialysate bag 122 is typically delivered to the patient and left in the patient until the subsequent PD treatment.

After completion of the PD treatment, the pistons 133A, 133B are retracted in a manner to disconnect the piston heads 134A, 134B from the dome-shaped members 161A, 161B of the cassette. The door 108 of the PD cycler is then opened and the cassette 112 is removed from the cassette compartment 114 and discarded.

While the control unit 139 of the PD cycler 102 has been described as being programmed to determine an adjustment volume based on a pressured measured by one of the pressure sensors 151A, 151B and to add that adjustment volume to the previously determined theoretical volume to determine the corrected volume, in certain implementations, the control unit simply accesses a look-up table that provides the corrected volume based on the position of the piston 133A, 133B (at the pressure that indicates the initial pressurization of the liquid) and the pressure in the isolated chamber at the end of the piston stroke (i.e., at the end of the inward stroke during drain and at the end of the outward stroke during fill). The look-up table can be populated with mathematically derived data and/or empirical data. In some implementations, the theoretical volume is determined mathematically in the manner described above and the correction factor is determined empirically in the manner described above. In certain implementations, both the theoretical volume and the correction factor are determined empirically using the methods discussed above.

While the PD system 100 has been described as including certain types of pressure transducers for measuring fluid pressure within the sensing chambers of the cassette, other types of pressure sensors can alternatively or additionally be used. In some implementations, for example, a Wheatstone bridge is used to determine the fluid pressure within the pump chamber 138A, 138B.

While the correction factor (K) has been described as varying across intermediate pressure ranges, in some implementations, the correction factor (K) can be a constant across each of the pressure ranges (i.e., the low pressure range, the intermediate pressure range, and the high pressure range). For example, a correction factor (K) of 0.01 can be used when the pressure (P) is between 30 mbar and 80 mbar during the drain phase, and a correction factor (K) of 0.0075 can be used when the pressure (P) is between −40 mbar and 40 mbar during the fill phase.

While the dialysate has been described as being pumped into the heater bag 124 from a single dialysate bag 122, dialysate can alternatively be pumped into the heater bag 124 from multiple dialysate bags 122. Such a technique may be advantageous, for example, where the dialysates in the bags 122 have different concentrations (e.g., different dextrose concentrations) and a desired concentration for treatment is intermediate to the concentrations of the dialysate in two or more of the bags 122.

While the piston heads 134A, 134B have been described as including spring-loaded latch mechanisms with sliding latches 145A, 145B that can be move radially inward and outward to allow those piston heads 134A, 134B to be mechanically connected to the dome-shaped members 161A, 161B of the cassette 112, piston heads of simpler construction that include no such sliding latches can alternatively be used in some cases. In some implementations, for example, each of the piston heads is a unitary structure that includes a peripheral flange that can be engaged with an annular projection of a dome-shaped member of a cassette in order to mechanically connect the piston head to the cassette and enable a fluid pumping process of the type described above to be carried out. In such implementations, the rear surface of the flange can be arranged at an angle of about 45 degrees to about 75 degrees (e.g., about 60 degrees) relative to the longitudinal axis of the piston to facilitate insertion of the piston head into the dome-shaped member. The peripheral flange of the piston head and/or the flange of the dome-shaped member can elastically deform as the piston head is advanced into the dome-shaped member. Examples of this type of piston head and dome-shaped member as well as other suitable types of piston heads and dome-shaped members are described in U.S. Patent Application Publication No. 2012/0271226, which is incorporated by reference herein.

Figure 10:
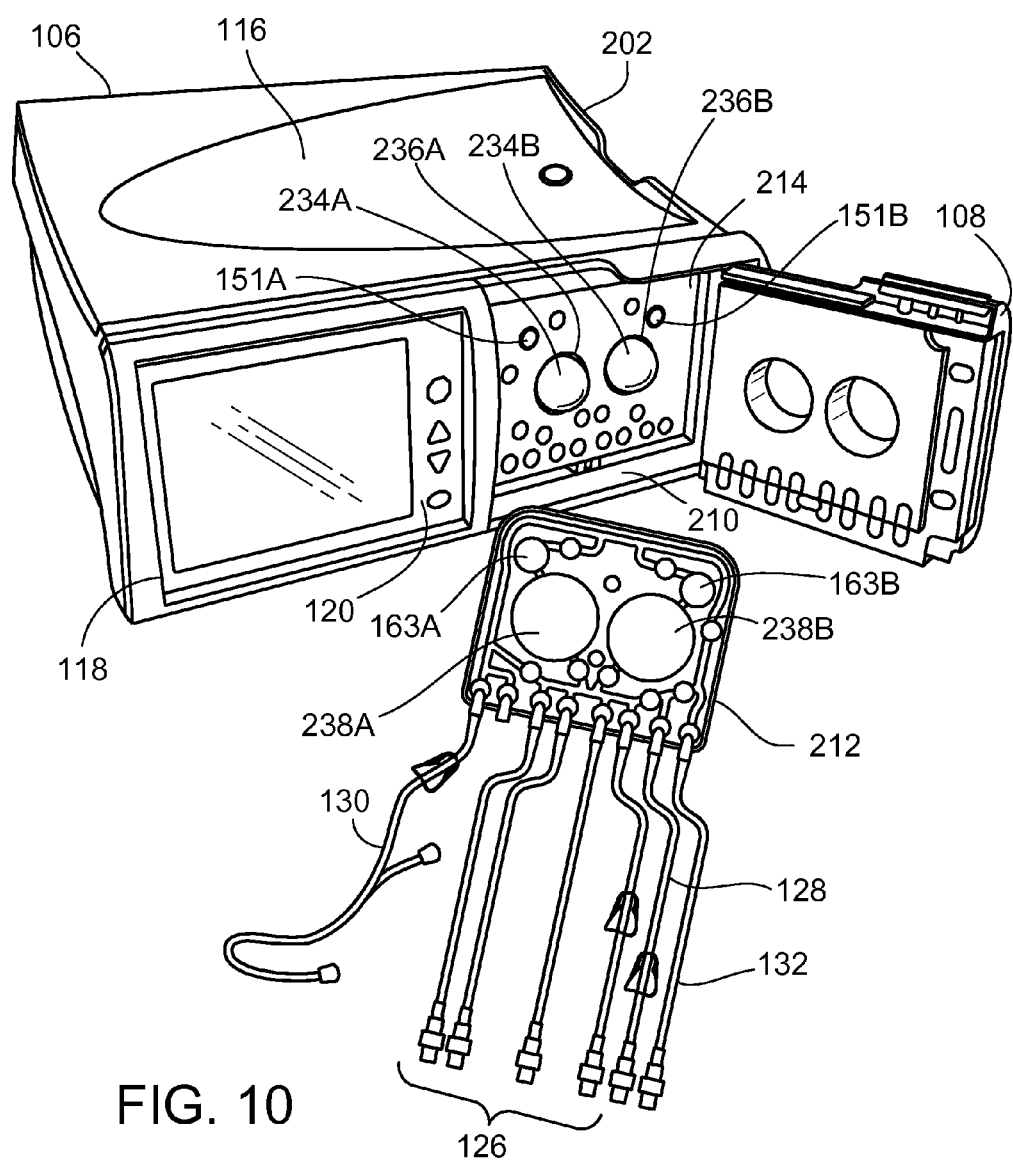
FIG. 10 is a perspective view of another PD system that includes a PD cassette and a PD cycler positioned atop a portable cart, with a door of the PD cycler in the open position to show the inner surfaces of the PD cycler that interface with the PD cassette during use.
Figure 11:
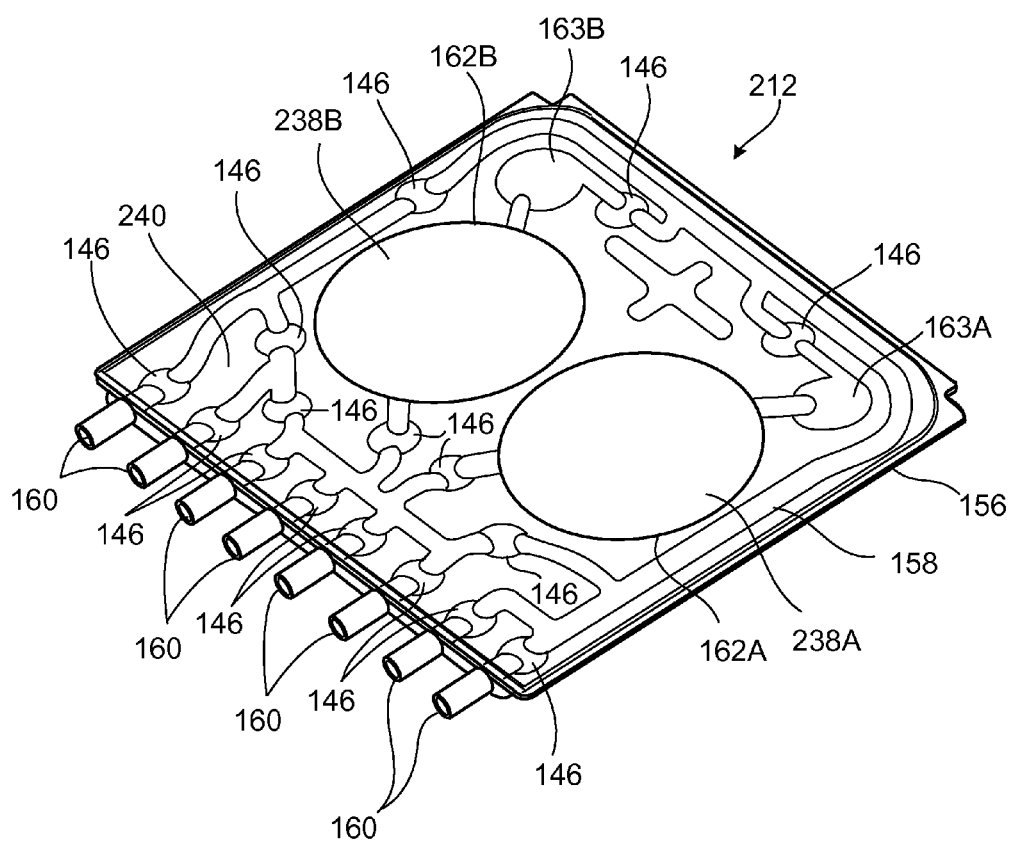
FIG. 11 is an exploded, perspective view the PD cassette of FIG. 10, which includes a membrane secured across a face of a rigid base to form pump chambers and fluid passages between the rigid base and the membrane.

While the piston heads and dome-shaped members of the cassette have been described above as being mechanically coupled to one another, other coupling techniques can be used. In some implementations, for example, the cassette includes a membrane that overlies the entire area of the pump chambers and that is driven by dome-shaped piston heads that generally conform to the recessed regions of the rigid base of the cassette. One example of such a system is illustrated in FIGS. 10 and 11. As show in FIGS. 10 and 11, the system includes a PD cycler 202 that is operable with a cassette 212. The PD cycler 202 has generally the same structure as PD cycler 102 described above except the PD cycler includes simpler dome-shaped piston heads 234A, 234B that include no latch mechanisms or other mechanical coupling mechanisms. A cassette interface 210 of the PD cycler includes annular openings 236A, 236B surrounding the piston heads 234A, 234B via which vacuum can be applied from a vacuum source (e.g., a vacuum pump or a negatively pressurized vacuum chamber) to a membrane 240 of the cassette 212 to hold the portions of the cassette membrane overlying the pump chambers in contact with the piston heads 234A, 234B when the cassette is disposed within a cassette compartment 214 during operation. Examples of such systems can be found in U.S. Patent Application Publication No. 2007/0112297, which is incorporated by reference herein.

During treatment, the piston heads 234A, 234B are reciprocated in much the same way as the piston heads 134A, 134B described above to draw fluid into and pump fluid out of pump chambers 238A, 238B of the cassette 212. As the piston heads 234A, 234B are retracted, the vacuum applied to the membrane 240 via the annular openings 236A, 236B helps to ensure that the portions of the membrane 240 overlying the pump chambers 238A, 238B retract at the same speed as the piston heads 234A, 234B. Because the outer diameter of those portions of the piston heads 234A, 234B that are in contact with the membrane 240 throughout most of the piston stroke are smaller than the maximum inner diameter of the recessed regions 162A, 162B of the rigid base 156 of the cassette 212, the membrane 240 will include annular portions that surround each of the piston heads 234A, 234B and overlie the pump chambers 238A, 238B. In much the same way as discussed above, these annular portions will tend to bulge outward and inward under certain conditions as fluid is pumped out of and drawn into the pump chambers 238A, 238B by advancing and retracting the piston heads 234A, 234B, respectively. For example, when the patient is positioned above the PD cycler 202 during the drain cycle, gravity assists the pumping operation to facilitate the transfer of spent dialysate from the patient to the pump chamber 238A. As a result, increased positive pressure is generated within the pump chamber 238A, causing the annular portion of the cassette membrane 240 to bulge outward. Similarly, when the patient is positioned below the PD cycler 202 during the fill cycle, gravity assists the pumping operation to facilitate the transfer of fresh dialysate from the pump chamber 238A to the patient. As a result, increased negative pressure is generated within the pump chamber 238A, causing the annular portion of the cassette membrane 240 to bulge inward. The volume of fluid that is pumped out of and drawn into the pump chambers 238A, 238B can be determined with greater accuracy by using the volume correction methods described herein, which account for the bulging of the annular portions of the membrane 240. Correction factors can be selected and applied in the manner discussed above to carry out such methods.

While the cassette interface 110 of the PD cycler 102 has been described as including locating pins 148 that help to ensure that the dome-shaped members of the cassette are aligned with the pistons 133A, 133B when the cassette is positioned in the cassette compartment 114, other structures or techniques can be used to ensure this alignment. In some implementations, for example, the cassette is placed against the door of the PD cycler with the hollow projections of the cassette disposed in recesses of the PD cycler's door, and the cassette is held in this position by retainer clips attached to the door. Upon closing the door, the pistons of the PD cycler align with the dome-shaped members of the cassette.

While the door 108 of each of the PD cyclers above has been described as including an inflatable pad that, when inflated, can press the cassette against the cassette interface, the inflatable pad can alternatively be positioned behind the cassette interface such that the cassette interface can be moved toward the door 108 to compress the cassette therebetween. Similarly, as an alternative to an inflatable pad, any of various mechanisms that can be operated to move a surface of the door 108 toward the cassette interface or vice versa can be used.

While the door 108 of the PD cyclers described above are shown as being positioned on a front face of the PD cyclers, the doors can alternatively be positioned at various other locations on the PD cyclers. For example, the doors could be positioned on a top face of the PD cycler such that the cassette is slid into the cassette compartment in a substantially horizontal orientation instead of a substantially vertical orientation. In some implementations, the door and the cassette interface of the PD cycler are positioned at an angle of about 10 to about 35 degrees to vertical when the PD cycler is rested on a horizontal surface. It has been found that this configuration makes it easier for the user to load the cassette into the cassette compartment.

While the cassettes discussed above have two pump chambers, the cassettes can alternatively have more or fewer than two pump chambers.

While each of the pump chambers of the cassettes described above has been described as including multiple ports, in certain implementations, the pump chambers include a single port that is used as both an inlet and an outlet. In such implementations, the inflatable valve members of the PD cycler that act on the valve portions of the cassettes would be activated and deactivated in a different sequence to allow fluid to be drawn into the pump chamber from a desired location and then to be forced out of the pump chamber to a desired location.

While certain PD cyclers above have been described as including a touch screen and associated buttons, the PD cyclers can alternatively or additionally include other types of screens and user data entry systems. In certain implementations, for example, the cycler includes a display screen with buttons (e.g., feather touch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While PD systems have been described, the methods described herein for determining a corrected volume of medical fluid pumped into and out of a chamber of a medical fluid cassette can be used in any of various other types of medical fluid pumping systems that use cassettes or cartridges. Other examples of medical fluid pumping systems with which the methods described herein can be used include hemodialysis systems, blood perfusion systems, and intravenous infusion systems.

Similarly, while many of the systems above have been described as being used to pump dialysate, other types of dialysis fluids can be pumped through the cassettes. As an example, in the case of cassettes used with hemodialysis machines, blood can be pumped through the cassettes. In addition, priming solutions, such as saline, can similarly be pumped through cassettes using the various different systems and techniques described above. Similarly, as an alternative to dialysis fluids, any of various other types of medical fluids can be pumped through the above-described cassettes depending on the type of medical fluid pumping machines with which the cassettes are used.

Other embodiments are within the scope of the following claims.

What is claimed is:

1. A method comprising:
   (a) pumping a medical fluid out of or drawing a medical fluid into a chamber of a medical fluid cassette such that a pressure of the medical fluid in the medical fluid cassette causes a membrane of the medical fluid cassette to bulge around a perimeter of a piston head;
   (b) calculating, by a processor, a theoretical volume of the medical fluid pumped out of or drawn into the chamber;
   (c) measuring the pressure of the medical fluid within the medical fluid cassette or within a fluid line connected to the medical fluid cassette;
   (d) selecting a correction factor based on the measured pressure, the correction factor corresponding to an amount of bulging of the membrane of the medical fluid cassette;
   (e) multiplying, by the processor, the theoretical volume of the medical fluid pumped out of or drawn into the chamber by the correction factor to determine an adjustment volume; and
   (f) determining a corrected volume of the medical fluid pumped out of or drawn into the chamber based on the adjustment volume.

2. The method of claim 1, wherein the adjustment volume is added to the theoretical volume to determine the corrected volume.

3. The method of claim 1, wherein the method comprises pumping the medical fluid out of the chamber of the medical fluid cassette by driving a piston against the membrane of the medical fluid cassette to decrease a volume of the chamber, calculating the theoretical volume of the medical fluid pumped out of the chamber, and multiplying the theoretical volume of the medical fluid pumped out of the chamber by the correction factor to determine the corrected volume of the medical fluid pumped out of the chamber.

4. The method of claim 1, wherein the method comprises drawing the medical fluid into the chamber of the medical fluid cassette by retracting a piston to pull the membrane of the medical fluid cassette to increase a volume of the chamber, calculating the theoretical volume of the medical fluid drawn into the chamber, and multiplying the theoretical volume of the medical fluid drawn into the chamber by the correction factor to determine the corrected volume of the medical fluid drawn into the chamber.

5. The method of claim 1, wherein calculating the theoretical volume of the medical fluid pumped out of or drawn into the chamber comprises determining a linear displacement of a piston.

6. The method of claim 1, further comprising isolating the chamber prior to measuring the pressure.

7. The method of claim 6, wherein isolating the chamber comprises closing valves adjacent first and second ports of the chamber.

8. The method of claim 6, wherein the pressure is measured a period of time after isolating the chamber.

9. The method of claim 6, wherein the chamber is isolated and the pressure is measured after drawing the medical fluid into the chamber.

10. The method of claim 6, wherein the chamber is isolated and the pressure is measured after pumping the medical fluid out of the chamber.

11. The method of claim 1, wherein the correction factor varies as a function of the measured pressure for measured pressures between a first pressure value and a second pressure value, the first pressure value being less than the second pressure value.

12. The method of claim 11, wherein the correction factor is a first constant for all measured pressures that are less than or equal to the first pressure value and the correction factor is a second constant for all measured pressures that are greater than or equal to the second pressure value.

13. The method of claim 1, wherein the correction factor has a first value if the measured pressure is less than or equal to a first pressure value and the correction factor has a second value if the measured pressure is greater than or equal to a second pressure value.

14. The method of claim 13, wherein the correction factor has a third value if the measured pressure is greater than the first pressure value and less than the second pressure value.

15. The method of claim 13, wherein the correction factor has the first value for all measured pressures less than or equal to the first pressure value, the first value being a constant.

16. The method of claim 13, wherein the correction factor has the second value for all measured pressures greater than or equal to the second pressure value, the second value being a constant.

17. The method of claim 1, wherein the medical fluid cassette is a peritoneal dialysis fluid cassette and the medical fluid is a dialysis fluid.

18. The method of claim 17, wherein the dialysis fluid is pumped out of the chamber and delivered to a peritoneal cavity of a patient.

19. The method of claim 17, wherein the dialysis fluid is drawn into the chamber from a peritoneal cavity of a patient.

* * * * *